US006628817B2

(12) United States Patent
Ishikawa et al.

(10) Patent No.: US 6,628,817 B2
(45) **Date of Patent: *Sep. 30, 2003**

(54) INSPECTION DATA ANALYZING SYSTEM

(75) Inventors: Seiji Ishikawa, Yokohama (JP); Masao Sakata, Ebina (JP); Jun Nakazato, Tokyo (JP); Sadao Shimoyashiro, Fujisawa (JP); Hiroto Nagatomo, Tokyo (JP); Yuzo Taniguchi, Higashimurayama (JP); Osamu Satou, Koganei (JP); Tsutomu Okabe, Kodaira (JP); Yuzaburo Sakamoto, Takasaki (JP); Kimio Muramatsu, Takasaki (JP); Kazuhiko Matsuoka, Takasaki (JP); Taizo Hashimoto, Takasaki (JP); Yuichi Ohyama, Isesaki (JP); Yutaka Ebara, Maebashi (JP); Isao Miyazaki, Isesaki (JP); Shuichi Hanashima, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 191 days.

This patent is subject to a terminal disclaimer.

(21) Appl. No.: 09/752,674

(22) Filed: Jan. 3, 2001

(65) Prior Publication Data

US 2001/0001015 A1 May 10, 2001

Related U.S. Application Data

(62) Division of application No. 08/958,095, filed on Oct. 27, 1997, now Pat. No. 6,185,322, which is a continuation of application No. 07/908,550, filed on Jun. 30, 1992, now Pat. No. 5,841,893, which is a continuation of application No. 07/550,942, filed on Jul. 11, 1990, now abandoned.

(30) Foreign Application Priority Data

Jul. 12, 1989 (JP) .......................................... 01-177934

(51) Int. Cl.$^7$ ................................................. G06K 9/00

(52) U.S. Cl. ......................... 382/141; 382/149; 348/86; 348/92; 356/237.1; 356/238.3

(58) Field of Search ................................ 382/141–145, 382/147, 149; 348/86, 92, 125, 126; 356/237.1, 238.3, 239.5; 358/406, 504

(56) References Cited

U.S. PATENT DOCUMENTS

| | | | |
|---|---|---|---|
| 3,751,647 A | 8/1973 | Maeder et al. | 713/401 |
| 3,873,972 A | 3/1975 | Levine | 382/243 |
| 4,189,711 A | 2/1980 | Frank | 382/242 |

(List continued on next page.)

FOREIGN PATENT DOCUMENTS

| | | |
|---|---|---|
| JP | 5619635 | 2/1981 |
| JP | 59228726 | 6/1983 |
| JP | 58165337 | 9/1983 |

(List continued on next page.)

OTHER PUBLICATIONS

Mital, et al. "An intelligent vision system for inspection of packaged ICa", IEEE, pp. 1003–1006, Apr. 1989.*

NEC Technical Report, vol. 46, No. 11, 1993 "Memory Failure Analysis with an Expert System".

(List continued on next page.)

*Primary Examiner*—Daniel G. Mariam
(74) *Attorney, Agent, or Firm*—Antonelli, Terry, Stout & Kraus, LLP

(57) ABSTRACT

The present invention provides data analysis stations respectively for a probing tester and an automatic particle inspection machine. And, in the data analysis station, the coordinates on which the disposition of the chips are described on a product basis are equal to those on which the locations of the defects are described. Further, the station provides a function of determining which of the chips each defect belongs to. These data analysis stations are connected through a communication line. The present invention is capable of analyzing the data on a chip basis, resulting in being able to grasp the relation between how the defects are caused on each chip and the product character of the chip.

25 Claims, 34 Drawing Sheets

U.S. PATENT DOCUMENTS

| | | | | | |
|---|---|---|---|---|---|
| 4,365,318 | A | | 12/1982 | Aichelmann | 382/243 |
| 4,449,818 | A | | 5/1984 | Yamaguchi et al. | 348/126 |
| 4,719,357 | A | | 1/1988 | Ayata et al. | 364/559 |
| 4,783,841 | A | | 11/1988 | Crayson | 382/243 |
| 4,817,184 | A | | 3/1989 | Thomason et al. | 382/141 |
| 4,851,902 | A | | 7/1989 | Tezuka et al. | 348/126 |
| 4,853,967 | A | * | 8/1989 | Mandeville | 382/147 |
| 4,881,863 | A | | 11/1989 | Braginsky | 414/225.01 |
| 4,894,790 | A | | 1/1990 | Yotsuya et al. | 382/147 |
| 4,908,871 | A | | 3/1990 | Hara et al. | 382/147 |
| 4,928,313 | A | | 5/1990 | Leonard et al. | 382/149 |
| 4,942,618 | A | | 7/1990 | Sumi et al. | 382/154 |
| 4,958,373 | A | | 9/1990 | Usami et al. | 382/149 |
| 5,070,532 | A | | 12/1991 | Faul et al. | 382/166 |
| 5,093,797 | A | | 3/1992 | Yotsuya et al. | 716/16 |
| 5,109,438 | A | | 4/1992 | Alves et al. | 382/243 |
| 5,216,726 | A | | 6/1993 | Heaton | 382/243 |
| 5,228,097 | A | | 7/1993 | Kumagai | 382/242 |

FOREIGN PATENT DOCUMENTS

| | | |
|---|---|---|
| JP | 63220513 | 9/1988 |
| JP | 6473241 | 3/1989 |
| JP | 1-122132 | 5/1989 |
| JP | 1-137641 | 5/1989 |
| JP | 1-151243 | 6/1989 |
| JP | 5967638 | 4/1984 |
| JP | 60171736 | 9/1985 |
| JP | 61243378 | 10/1986 |
| JP | 63135848 | 11/1986 |
| JP | 6276712 | 4/1987 |
| JP | 62169342 | 7/1987 |
| JP | 62220839 | 9/1987 |
| JP | 62276441 | 12/1987 |
| JP | 6366446 | 3/1988 |
| JP | 6366447 | 3/1988 |
| JP | 63110744 | 5/1988 |
| JP | 63135848 | 6/1988 |

OTHER PUBLICATIONS

Przybyla et al., "A Fully Integrated Photolithography Workcell", May 1989, 100–107, IEEE, Intl. Semiconductor Mfg. Science Symposium, 1989.

Henderson, "A Production Fab Defect Reduction Program", May 1989, 58–60, IEEE, Intl. Semiconductor Mfg. Science Symposium, 1989.

* cited by examiner

F I G. 2
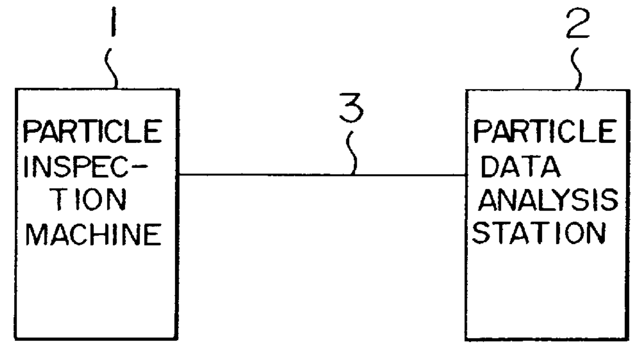
F I G. 3
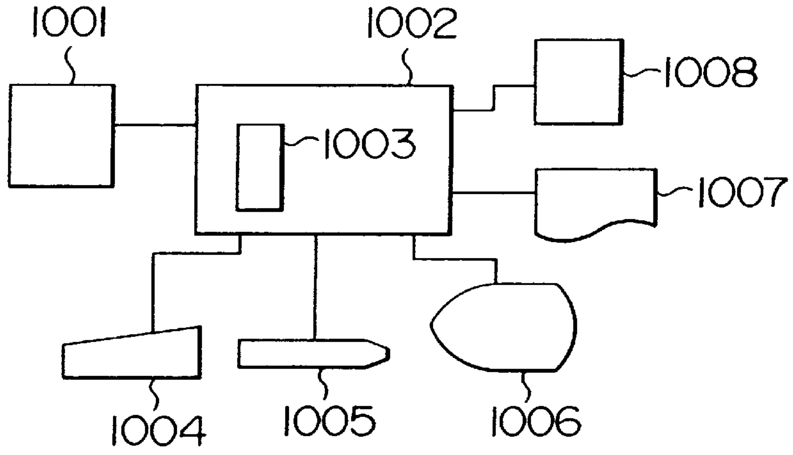
F I G. 4
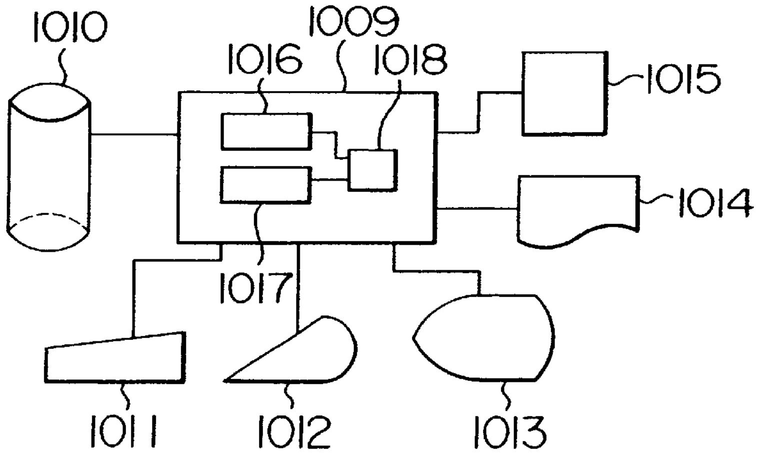

FIG. 5A

LOT UNIT DATA TABLE

| PRODUCT NAME (5001) | INSPECTED PROCESS NAME (5002) | LOT NUMBER (5003) | WAFER SIZE (5004) | INSPECTION DATE (5005) | INSPECTION TIME (5006) |
|---|---|---|---|---|---|
| HM001 | A | A01 | 5 | 88/12/01 | 12:45 |
| HM001 | B | A02 | 5 | 89/01/08 | 16:30 |
| HM002 | C | B01 | 6 | 89/02/03 | 17:40 |

FIG. 5B

WAFER UNIT DATA TABLE

| INSPECTED PROCESS NAME (5007) | LOT NUMBER (5008) | WAFER NUMBER (5009) | PARTICLE NUMBER (5010) |
|---|---|---|---|
| A | A01 | 1 | 1 |
| A | A01 | 2 | 10 |
| A | A01 | 3 | 100 |

FIG. 5C

PARTICLE UNIT DATA TABLE

| INSPECTED PROCESS NAME (5011) | LOT NUMBER (5012) | WAFER NUMBER (5013) | PARTICLE COORDINATE X (5014) | PARTICLE COORDINATE Y (5015) | PARTICLE SIZE (5016) |
|---|---|---|---|---|---|
| A | A01 | 1 | 10500 | 10270 | S |
| A | A01 | 2 | 25000 | 8700 | L |
| A | A01 | 2 | 34510 | 28765 | L |

| 5017 | 5018 | 5019 | 5020 | 5021 | 5022 | 5023 |
|---|---|---|---|---|---|---|
| PRODUCT NAME | WAFER SIZE | CHIP VERTICAL WIDTH | CHIP HORIZONTAL WIDTH | MATRIX VERTICAL WIDTH | MATRIX HORIZONTAL WIDTH | NON-USE CHIP LOCATION |
| HM001 | 5 | 20000 | 12000 | 5 | 9 | (3,3)(7,3) |
| HM002 | 6 | 10000 | 8000 | 14 | 17 | (3,3)(4,3) |
| HM003 | 6 | 10000 | 10000 | 14 | 14 | (3,3)(4,3) |

| 5024 | 5025 |
|---|---|
| PRODUCT NAME | LOT NUMBER |
| HM001 | 20 |
| HM002 | 15 |
| | |

| PRODUCT NAME | PROCESS NAME | LOT NO. | WAFER NO. | INSPECTION DATE | PARTICLE NUMBER | L | M | S | OPERATOR NAME |
|---|---|---|---|---|---|---|---|---|---|
| | | | | | | | | | |

1037 1038 1039 1040 1041 1042 1043 1044 1045 1046

1035
1036
1047

LOT NO. LIST

PRODUCT NAME ( )    PROCESS NAME ( )    REGISTERED LOT ( )

| No. | LOT NO. | No. | LOT NO. |
|---|---|---|---|
| 21 | C45 | 22 | C51001 |
| 23 | C51002 | 24 | C51002 |
| 25 | C51003 | 26 | C51007 |
| 27 | C51008 | 28 | C51009 |
| 29 | C51012 | 30 | C51016 |
| 31 | C51017 | 32 | C51021 |
| 33 | C51023 | 34 | C51027 |
| 35 | C51028 | 36 | C51031 |
| 37 | C51034 | 38 | C51042 |
| 39 | C51044 | 40 | C51045 |

1047

1048  1049  1050

WAFER NO. LIST

PRODUCT NAME ( )    PROCESS NAME ( )    REGISTERED WAFER 25

| No. | WAFER NO. | No. | WAFER NO. |
|---|---|---|---|
| 1 | 1 | 2 | 2 |
| 3 | 3 | 4 | 4 |
| 5 | 5 | 6 | 6 |
| 7 | 7 | 8 | 8 |
| 9 | 9 | 10 | 10 |
| 11 | 11 | 12 | 12 |
| 13 | 13 | 14 | 14 |
| 15 | 15 | 16 | 16 |
| 17 | 17 | 18 | 18 |
| 19 | 19 | 20 | 20 |

1047

1048  1049  1050

| No. | OPERATOR NAME | No. | OPERATOR NAME |
|---|---|---|---|
| 1 | A.KUNO | 2 | AKASHI |
| 3 | AKIE | 4 | AKIE·AND. |
| 5 | AKIE·CHAN | 6 | C.NIZUGUC |
| 7 | DECE·SIN2 | 8 | H.NAGAISH |
| 9 | KAMA | 10 | KUNO |
| 11 | M.SAITO | 12 | MIZUGUCHI |
| 13 | MOKUDAI | 14 | N.OKAMOTO |
| 15 | NAKAJIMA | 16 | OKAMOTO |
| 17 | R.AKASHI | 18 | SATOU |
| 19 | T.KAMA | 20 | T.YONEOKA |

| PRODUCT NAME | | |
|---|---|---|
| PROCESS NAME | | |
| LOT NO. | | |
| WAFER NO. | | |
| INSPECTION DATE | | |
| PARTICLE NUMBER | | |
| L | | |
| M | | |
| S | | |
| OPERETOR NAME | | |

F I G. 25
| PRODUCT NAME (5026) | CHIP LOCATION X (5027) | CHIP LOCATION Y (5028) | AREA CATEGORY (5029) |
|---|---|---|---|
| HM001 | 1 | 5 | A |
| HM001 | 1 | 6 | A |
| HM001 | 1 | 7 | B |
| HM001 | 1 | 8 | B |
| HM001 | 2 | 5 | C |
| HM001 | 2 | 6 | C |
| HM001 | | | |
F I G. 26
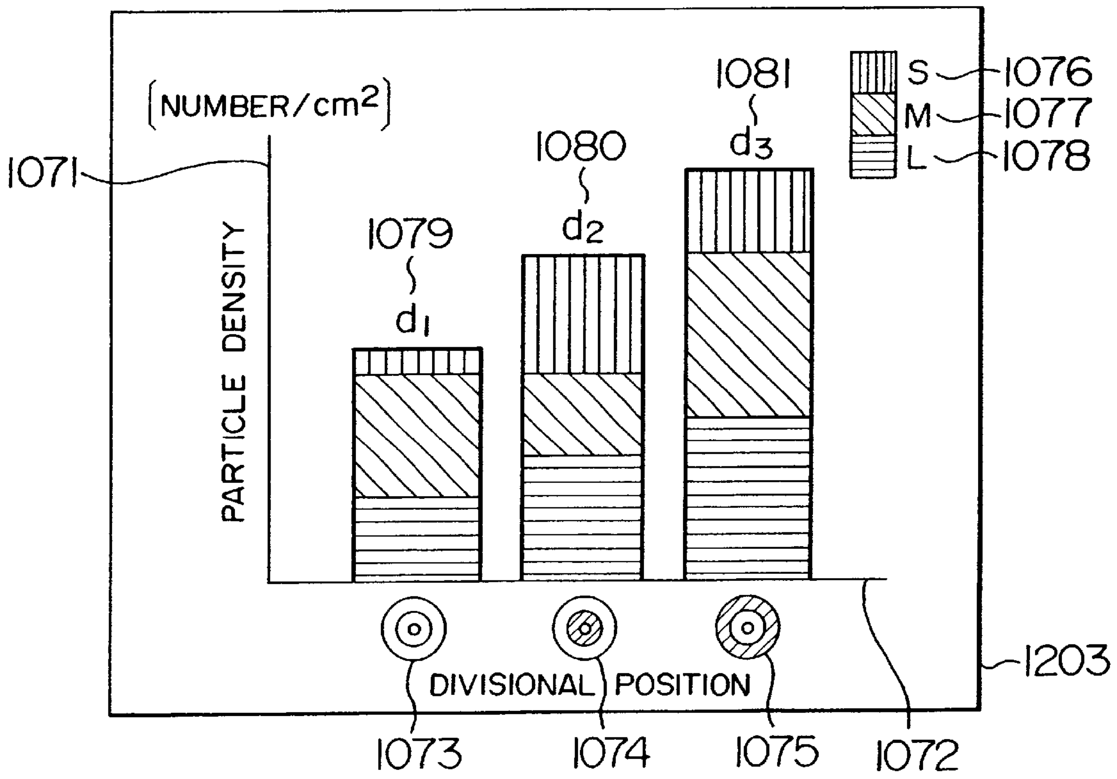

F I G. 27
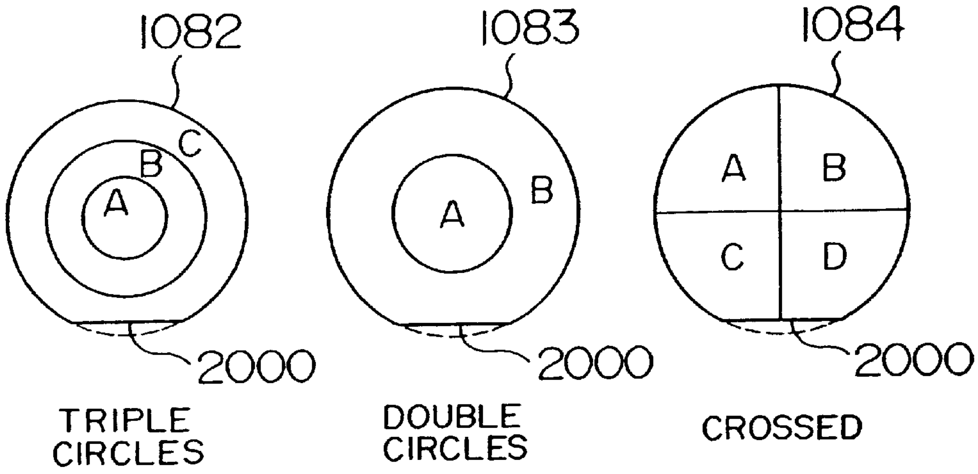
F I G. 28
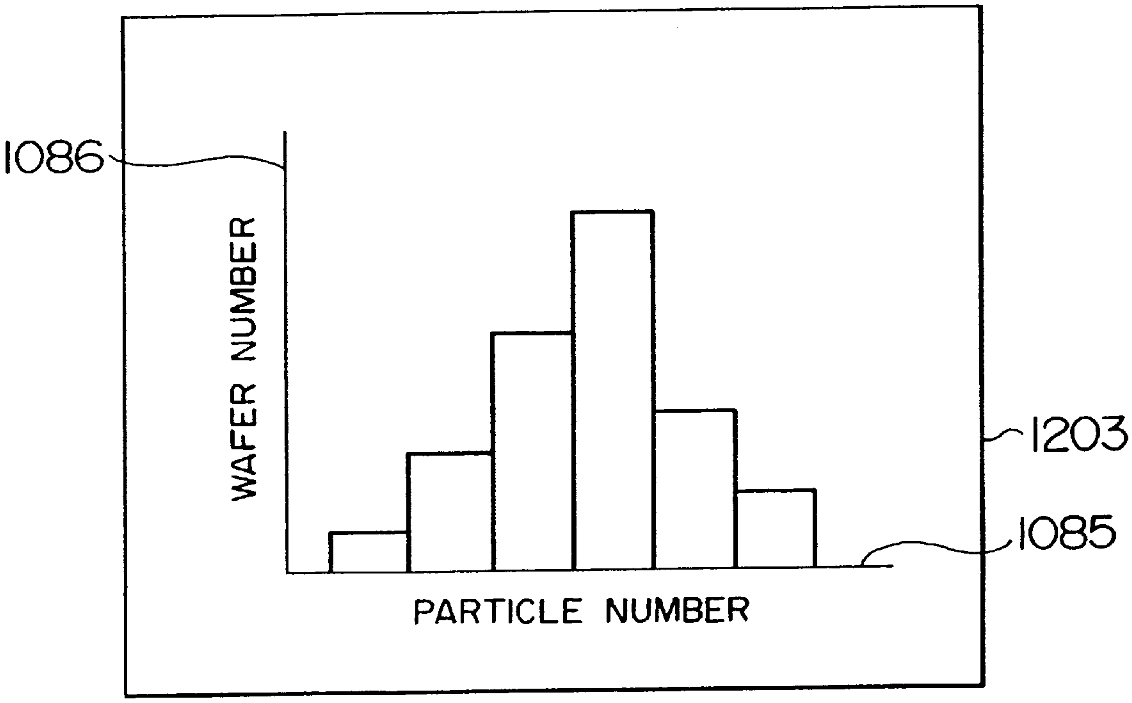

| PROCESS NUMBER (5030) | PARTICLE NUMBER (5031) | PARTICLE X COORDINATE (5032) | PARTICLE Y COORDINATE (5033) |
|---|---|---|---|
| 1 | 1 | 5112 | 1022 |
| 1 | 2 | 6811 | 7863 |
| 1 | 3 | 7005 | 12450 |
| 1 | 4 | 9543 | 18635 |
| 1 | 5 | 9611 | 19687 |

FIG. 38A

LOT UNIT DATA TABLE

| PRODUCT NAME (5034) | INSPECTED PROCESS NAME (5035) | LOT NUMBER (5036) | WAFER SIZE (5037) | INSPECTION DATA (5038) | INSPECTION TIME (5039) |
|---|---|---|---|---|---|
| HM001 | A | A01 | 5 | 88/12/01 | 16:40 |
| HM001 | B | A02 | 5 | 89/01/08 | 10:30 |
| HM002 | C | A03 | 6 | 89/02/03 | 11:20 |

FIG. 38B

LOT UNIT DATA TABLE

| INSPECTED PROCESS NAME (5040) | LOT NUMBER (5041) | WAFER NUMBER (5042) | DEFECTS NUMBER (5043) | CRITICAL DEFECTS NUMBER (5044) | DEFECTS CHIP NUMBER (5045) |
|---|---|---|---|---|---|
| A | A01 | 1 | 4 | 3 | 4 |
| A | A01 | 2 | 2 | 1 | 2 |
| A | A01 | 3 | 6 | 2 | 5 |

FIG. 38C

DEFECTS UNIT TABLE

| INSPECTED PROCESS NAME (5046) | LOT NUMBER (5047) | WAFER NUMBER (5048) | DEFECTS COORDINATE X (5049) | DEFECTS COORDINATE Y (5050) | KIND (5051) | CRITI-CALITY (5052) |
|---|---|---|---|---|---|---|
| A | A01 | 1 | 12050 | 14000 | 1 | 1 |
| A | A01 | 1 | 5248 | 18600 | 5 | 0 |
| A | A01 | 1 | 27000 | 17471 | 11 | 0 |

5053 5054

| PRODUCT NAME | WATER NUMBER |
|---|---|
| HM001 | 10 |
| HM002 | 7 |
| HM003 | 16 |
| | |

FIG. 48A

PROBING TEST LOT DATA TABLE

| PRODUCT NAME (1146) | LOT NO. (1147) | INSPECTION DATE (1148) | INSPECTION TIME (1149) | OPERATOR NAME (1150) |
|---|---|---|---|---|
| HM001 | A01 | 89/02/05 | 11:10 | SATO |
| HM002 | A02 | 89/02/18 | 10:40 | HASHIMOTO |
| | | | | |

FIG. 48B

PROBING TEST WAFER DATA TABLE

| LOT NO. (1151) | WAFER NO. (1152) | CHIP LOCATION X (1153) | CHIP LOCATION Y (1154) | GOOD, DETECTIVES (1155) | WAFER YIELD (1156) |
|---|---|---|---|---|---|
| A01 | 1 | 4 | 6 | 0 | 100.0 |
| A01 | 1 | 11 | 4 | 0 | 100.0 |
| | | | | | |
| | | | | | |
| A01 | 2 | 4 | 6 | 0 | 99.0 |
| A01 | 2 | 5 | 8 | 1 | 99.0 |
| | | | | | |

FIG. 49

| PRODUCT (1157) | ESTIMATED PRODUCT NUMBER (1158) |
|---|---|
| HM001 | 250 |
| HM002 | 150 |
| HM003 | 300 |

F I G. 55
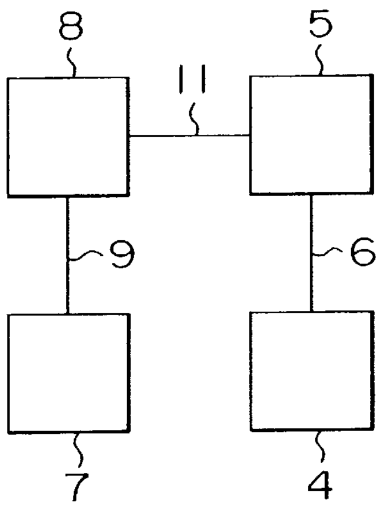
F I G. 56
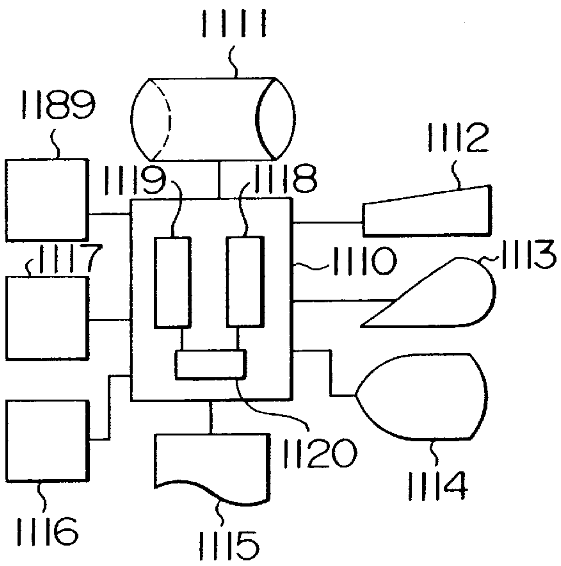
F I G. 57
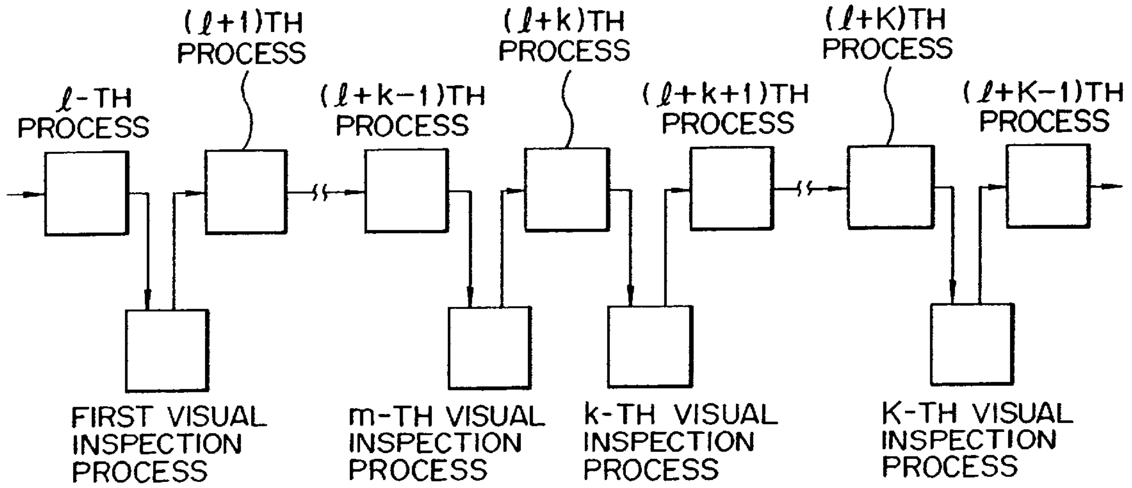

INSPECTION DATA ANALYZING SYSTEM

CROSS-REFERENCE TO RELATED APPLICATIONS

This application is a divisional of application Ser. No. 08/958,095, filed on Oct. 27, 1997 (now U.S. Pat. No. 6,185,322 issued Feb. 26, 2001), which is a continuation of application Ser. No. 07/908,550, filed on Jun. 30, 1992 (now U.S. Pat. No. 5,841,893 issued Nov. 24, 1998); which is a continuation of application Ser. No. 07/550,942, filed on Jul. 11, 1990 (now abandoned).

BACKGROUND OF THE INVENTION

The present invention concerns visual inspection for a product or a part being manufactured and more particularly to an inspection data analyzing system which is capable of inspecting defects or particles on a surface of the product or part and analyzing the inspection data.

In the manufacture of a semiconductor device or the like, product defects often result from particles or other defects existing on a surface of a work piece (noting that particles are one type of defect that can occur). It is, therefore, necessary to quantitatively inspect particles or other defects for normally monitoring if a problem occurs in the manufacturing machine or the environment around it. And, it is necessary to grasp how the particles or other defects have an adverse effect on yield and take effective measures for the particles or other defects for improving the yield. Hereinafter, the terms “particles or other defects” will sometimes be generally referred to as “defects”, but when specific reference is made only to particles, it will be identified as such.

As an example, the use of an automatic visual inspection machine for data analysis in the manufacture of semiconductors has been disclosed in an article entitled “How does the automatic wafer inspection improve a yield?”, Solid State Technology (Japanese Version), July 1988, pages 44 to 48. The visual inspection is carried out for wafers in more than one manufacturing process. Hence, the inspection data includes data for managing the inspection data itself. The managing data contains a product name of a inspected wafer, a lot number, a wafer number, and an inspected process, data, and time, for example. It is necessary to analyze not only the inspection data but also the managing data. The conventional visual inspection machine includes a function of measuring sizes of defects and where the defects are located on a wafer coordinate, a function of measuring the number of defects existing on a wafer, and a means for allowing an operator to determine a category of defects, and the like. The machine inspects the change of the number of defects on each wafer, the distribution of defect frequency on a wafer-size basis, and the like. Further, the machine serves to analyze the correlation between the number of defects on each wafer (defects density) and the yield of the wafer as well.

And, each wafer has to be identified in more than one visual inspection process in the data analysis. Conventionally, the operator has visually recognized a wafer number. To reduce the burden of this operation, an automatic particle inspection machine having a means for automatic recognition of a wafer number has been disclosed in JP-A-63-213352.

Known automatic visual inspection machines have been categorized into two groups. One is referred to as an automatic particle inspection machine which is an inspection machine employing a light-scattering system. This machine serves to inspect particles existing on a wafer. It is thus unable to always inspect defects other than particles. The other group is an inspection machine employing a pattern recognition system. It is referred to as an automatic visual inspection machine or an automatic defect inspection machine, which has a function of accurately recognizing other defects in addition to particles. The automatic visual inspection machine needs an inspection time which is about 1000 times as long as the time required by the automatic particle inspection machine. The former machine can thus inspect a far smaller number of wafers than the latter. For monitoring how defects are caused in a mass production line, two methods are provided. The first method is to restrict the processes to be visually inspected to a specific process (Solid State Technology (Japanese Version), July 1988, pages 44 to 48). The second method is to take the steps of matching the particle inspection data to the visual inspection data over all the processes and machines, checking the correlation between particles and defects, and presuming how defects are caused on the particle inspection data (Semiconductor World, May 1989, pages 118 to 125). Further, in analyzing data, these methods require an operator who serves to analyze data, because there exist a lot of data and various kinds of data analysis methods in analyzing data.

The conventional method is uncapable of grasping how defects are caused on each chip. Hence, they can merely perform correlation analysis between the number of defects per wafer and a yield. That is, these methods have a disadvantage that they cannot grasp the relation between defects per wafer and a product character. In addition, one semiconductor for one wafer is provided at this time, while two or more semiconductors for one wafer will be provided in future. It is necessary to enhance the data processing unit from a wafer unit to a chip-unit basis. A new data analysis technique is expected accordingly.

And, for inspecting how many defects are caused in a mass production line, the foregoing first method is designed to determine the process to be visually inspected on the basis of the knowledge of an operator and the result of a probing test. The foregoing second method requires large labor for matching the particle inspection data to the visual inspection data over all the processes and machines.

Moreover, an operator who is mainly in charge of maintaining and managing the manufacturing machine does not have spare time to analyze the inspection data of a wafer given by his or her machine. Hence, the operator requests the data analysis of another operator who is mainly in charge of it. However, novel data analysis method and means are expected which anyone can operate easily and quickly and which serve to output the analyzed data.

SUMMARY OF THE INVENTION

It is therefore an object of the present invention to provide an inspection data analysis system which is capable of analyzing data per chip for the purpose of grasping the relation between the occurrence condition of defects per chip and the product character of each chip.

And, it is a further object of the present invention to provide an inspection data analyzing system which is capable of easily determining a manufacturing process which causes problems and the contents or the problems.

It is another object of the present invention to provide an inspection data analyzing system which is capable of monitoring the overall production line and efficiently inspecting the quantity of caused defects in a mass production line.

To achieve the foregoing objects, the present invention offers a probing tester, an automatic particle inspection machine, and an automatic visual inspection machine respectively having data analysis stations. Each data analysis station has chip arrangement information for each product and serves to describe the locations of defects on the coordinate system on which the chip disposition is described. And, the station provides a function for determining on which chip each defect is caused. These data analysis stations are linked with a communication line.

Further, for inspecting the quantity of caused defects in the mass production line, the particle inspection machine operated at a higher inspection speed employs the step of monitoring the overall manufacturing line, inspecting the portions around caused defects, and monitoring the quantity of caused defects.

And, in order for anyone to use the machine, the data analysis station is designed to offer a routine data retrieval method, a routine operation method, and a routine analysis result output format.

As mentioned above, each data analysis station provides chip disposition information, a function of describing the locations of caused defects on the coordinate system on which the chip disposition is described, and a function of determining on which chip each defect is caused. It is thus possible to grasp how particles are attached and defects are caused on each chip. By linking these data analysis stations with a communication line, therefore, the data analysis station for probing test data sends the probing data to the station for particles and defects data so that the latter station can inspect the relation between the condition of caused defects on each chip and the probing test result (product character). As will be understood from the above description, the present invention is designed so that the particle inspection machine operating at a higher inspection speed serves to monitor the overall manufacturing line and the visual inspection machine serves to inspect portions around caused particles for inspecting the quantity of caused defects. Hence, this invention is capable of efficiently inspecting the quantity of caused defects in a mass production line.

Further, in analyzing data, as mentioned above, this invention has a routine data retrieval method, a routine operating method, and a routine output format, so that anyone can analyze the data and obtain clear outputs.

BRIEF DESCRIPTION OF THE DRAWINGS

FIG. 2 is a diagram showing partial arrangement of a particle inspection system shown in FIG. 1;

FIG. 3 is a diagram showing arrangement of a particle inspection machine shown in FIG. 2;

FIG. 4 is a diagram showing a particle data analysis station shown in FIG. 2;

FIG. 5A is a chart showing a data table for each lot in a particle database;

FIG. 5B is a chart showing a data table for each wafer in the particle database;

FIG. 5C is a chart showing a data table for each particle in the particle database;

FIG. 25 is a chart showing a map information file;

FIG. 26 is a chart showing a particle density to divided locations of the wafer, used for analyzing the distribution of particles;

FIG. 27 is a view showing a pattern on which the wafer is divided;

FIG. 28 is a chart showing how particles are distributed in a wafer;

FIG. 38A is a chart showing a data table for each lot in the defects database shown in FIG. 37;

FIG. 38B is a chart showing a data table for each wafer in the defects database shown in FIG. 37;

FIG. 38C is a chart showing a data table for each defect in the defects database shown in FIG. 37;

FIG. 48A is a chart showing a probing test lot data table in a probing test database shown in FIG. 46;

FIG. 48B is a chart showing a probing test wafer data table in the probing test database shown in FIG. 46;

FIG. 49 is a chart showing an analysis data auxiliary file;

FIG. 55 is a diagram showing a visual inspection machine, which is part of the system shown in FIG. 1;

FIG. 56 is a diagram showing arrangement of a defects data analysis station;

FIG. 57 is a diagram showing a relation between a particle inspection process and a visual inspection process;

DESCRIPTION OF THE PREFERRED EMBODIMENTS

Figure 1:
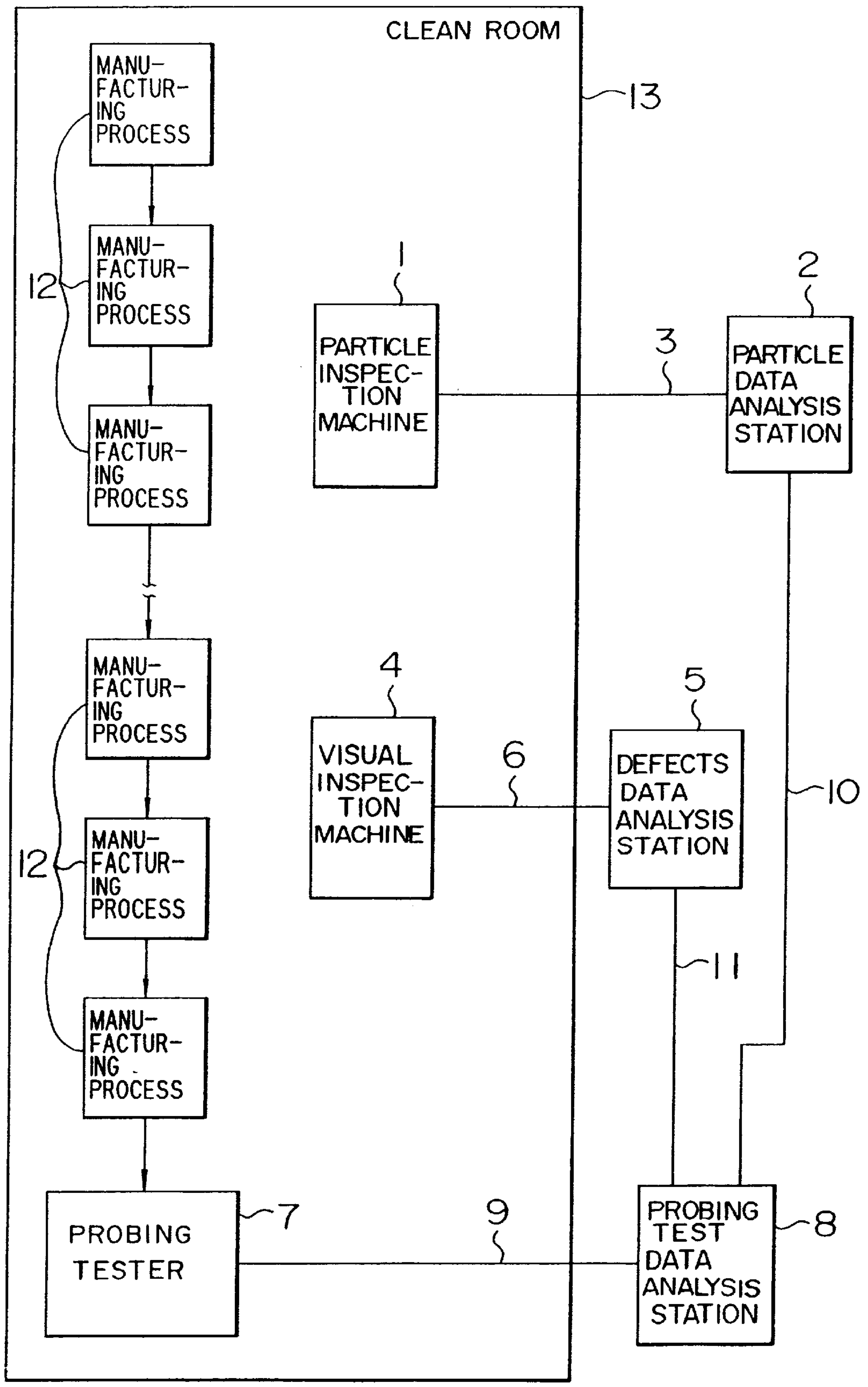
FIG. 1 is a diagram showing overall arrangement of an inspection data analysis system according to an embodiment of the present invention.

The overall arrangement of the system will be described with reference to FIG. 1. This embodiment is a manufacturing line for semiconductor devices to which the present invention is applied. The reference numeral 12 denotes a semiconductor device manufacturing process. It is normally located in a clean room 13 in which the environment is kept clean. In the clean room 13, there are provided a particle inspection machine 1 having a function of measuring the number of defects existing on a product wafer and the locations of the defects on a wafer coordinate system, a visual inspection machine 4 having functions of measuring the number of defects existing on a product wafer and the locations of the defects on the wafer coordinate system and of recognizing a category of defects (the visual inspection machine 4 simply referred hereinafter indicates this inspection machine. This inspection machine serves to inspect general defects such as pattern defects, particles, and discoloration defects.), and a probing tester 7 for testing the product character of a chip. These machines are disclosed in Kubota et. al.; "Particle and Visual Inspection Machines" Hitachi Critique, 71 volumes, No. 5, pages 55 to 62, for example. The particle inspection machine 1, the visual inspection machine 4, and the probing tester 7 respectively provide a particle data analysis station 2, a defects data analysis station 5, and a probing test data analysis station 8, which are all installed outside of the clean room 13. The inspection machines 1, 4, 7 are linked with the analysis stations 2, 5, 8 through communication lines 3, 6, 9. Further, the particle analysis station 2 is linked with the probing test data analysis station 8 through a communication line 10 and the defects analysis station 5 is linked with the probing test data analysis station 8 through a communication line 11.

On the semiconductor device manufacturing line, wafers are transported in lots. For particle- or visual-inspecting these wafers, after finishing the process to be particle- or visual-inspected, each lot is carried to the particle inspection machine 1 or the visual inspection machine 4 in which some or all wafers contained in the lot are inspected. For carrying out the particle or visual inspection, it is possible to employ a method for determining a subject process on the basis of the operator's knowledge or a method for determining a process to be visually inspected on the basis of the particle-inspecting result as mentioned below. In the particle or visual inspection, data is supplied to each inspection machine. The data contains a lot number of a wafer, a wafer number, an inspection day and time, a process located immediately before the inspection, and the like. The process-completed wafers are carried to the probing tester 7 at each lot, in which tester 7 all the wafers contained in the lot are subject to a probing test. Herein, the lot number of a wafer, the wafer number, and the inspection day and time are supplied to the probing tester 7. The particle data analysis station 2 and the defects data analysis station 5 contain information about how chips are disposed on a wafer for each product. Based on the information, these stations serve to determine which chip the inspected defects belong to on the basis of the locations of the inspected defects placed on the chip coordinate system and count how many defects are brought about on each chip. Based on the number of defects existing on a wafer, the location coordinates of the defects, and the number of defects on a chip, the particle inspection data analysis station 2 and the visual inspection data analysis station 5 serve to carry out the analysis described hereinafter. Further, the particle inspection data analysis station 2 and the visual inspection data analysis station 5 serve to carry out the analysis described hereinafter on the basis of the number of defects existing on a wafer, the location coordinates of defects, the number of defects on a chip, and the data about a product character read from the probing test data analysis station 8.

Next, referring to FIG. 2, there will be described an arrangement of the particle inspection machine 1 and the particle inspection data analysis station 2 included in the inspection data analysis system of FIG. 1.

The present system consists of the particle inspection machine 1 for inspecting particles on a wafer and the particle data analysis station 2 for analyzing data sent from the particle inspection machine 1. The former machine 1 is connected to the latter station 2 with a communication line 3.

FIG. 3 illustrates the arrangement of the particle inspection machine 1. The particle inspection machine 1 comprises a particle sensor 1001, a particle sensing signal processing unit 1002, a memory 1003, a keyboard 1004 served as an input unit, a bar-code reader 1005, a CRT 1006 and a printer 1007, both of which are served as an output unit, and an external communication unit 1008 for carrying out the communication with the particle data analysis station 2. The machine 1 has a function of defining the two-dimensional location coordinates of particles to be inspected on a wafer, the sizes of the particles, and the number of particles existing on the wafer.

FIG. 4 illustrates the arrangement of the particle data analysis station 2. The particle data analysis station 2 comprises a particle data processing unit 1009, a particle database 1010 for saving the inspection data sent from the particle inspection machine 1, a keyboard 1011 served as an input processing unit, a mouse 1012, a CRT 1013 and a printer 1014 served as an output unit, an external communication unit 1015 for carrying out communication with the particle inspection machine, a memory 1016 located inside of the particle data processing unit, an internal harddisk 1017, and a CPU 1018.

In wafer inspection, the particle management data is supplied to the particle inspection machine 1 using the keyboard 1004 or the bar-code reader 1005. The data contains an inspected wafer name, an inspected process name, a lot number, a wafer number, inspection data, an inspection time, and an operator ID. Further, the particle inspection data is also saved together with the particle management data. This particle inspection data contains the number of the particles existing on the inspected wafer, the location coordinates of the particles, and the sizes of the particles, which are measured in the particle inspection machine 1. Each particle can be categorized in L, M, and S sizes in larger order when saved.

The form of the particle database 1010 is illustrated and described with reference to FIG. 5. The particle database 1010 includes three databases referred to as a lot unit data table (see FIG. 5A), a wafer unit data table (see FIG. 5B), and a particle unit data table (see FIG. 5C). The lot unit data table serves to save particle management data 5001, 5002, 5003, 5005, 5006 and a wafer size 5004. The wafer unit data table serves to save a lot number 5008, a wafer number 5009, and the number of particles 5010 existing on the inspected wafer contained in the particle inspection data. The particle data processing unit 1009 saves a map information file and a lot number management file for each product in the internal harddisk 1017. The map information file contains a wafer size for each product, a chip horizontal width 1019, a chip vertical width 1020, a matrix vertical width 1022, a matrix horizontal width 1023, and non-use chip positions 1024, 1025 registered therein (see FIG. 6). The lot number management file for each product contains a lot number 5025 for each product registered therein. The formats of the map information files will be illustrated with reference to FIG. 7. The format of the lot number management file for each product will be illustrated with reference to FIG. 8.

Figure 10:
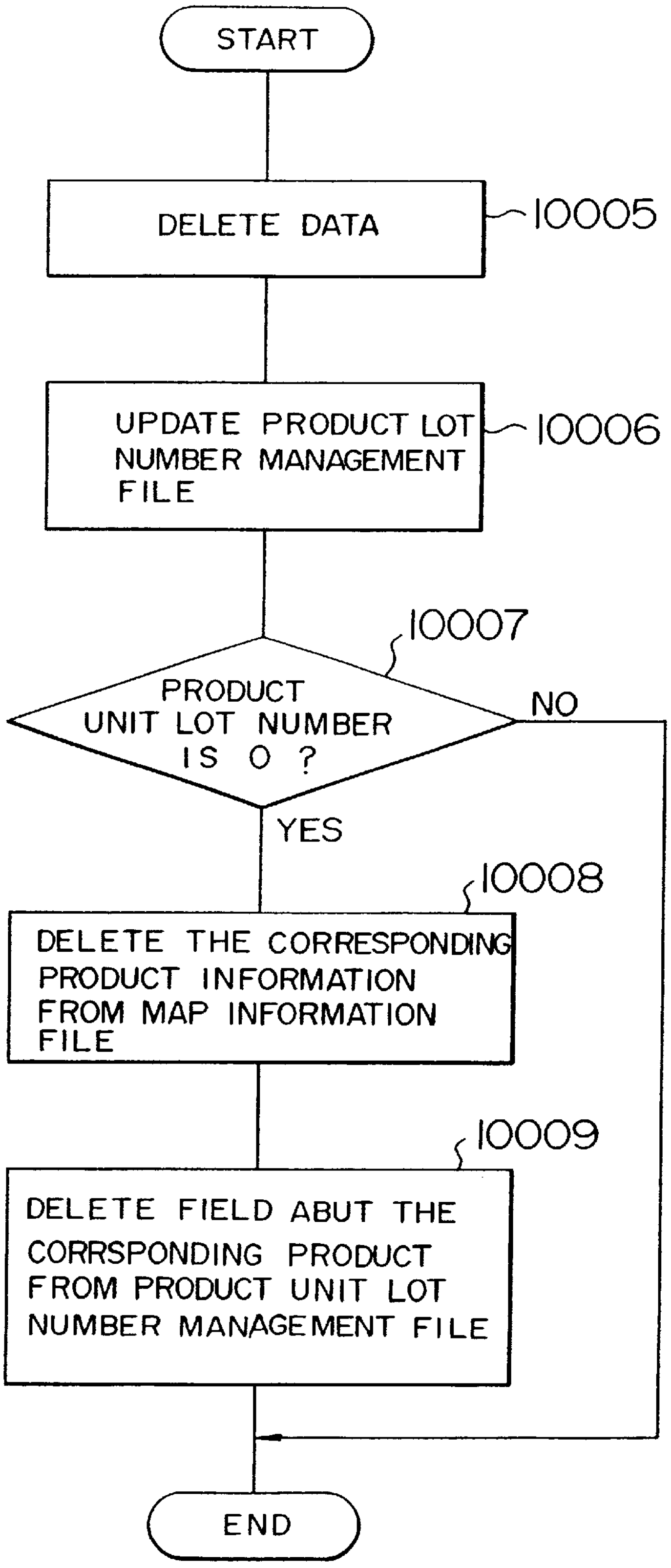
FIG. 10 is a flowchart showing the procedure involved with deletion of data.

Next, how to register the data will be described with reference to FIG. 9. After the particle inspection machine 1 finishes the inspection of one lot (step 10001), it sends the particle management data and the particle inspection data to the particle data analysis station 2 through the communication line 3 (step 10002). When the particle management data and the particle inspection data for one lot are registered in the particle database 1010 (step 10003), the particle data processing unit 1009 increments by one the lot number for each product in the lot number management file for each product (step 10004). Then, the data deletion procedure is illustrated in FIG. 10. An analysis operator routinely maintains the particle database 1010 and deletes the data about the lot he or she determines unnecessary (step 10005). When the one-lot data is deleted from the particle database 1010, the particle data processing unit 1009 decrements by one the lot number for each product in the lot number management file for each product (step 10006). Then, in the product unit lot number management file, it is determined if the product unit lot number is zero (step 10007). If yes, the map information file about the product is deleted and then the file about the product in the product unit lot number management file is deleted (step 10008). If no at the step 10007, the procedure is directly finished.

Figure 11:
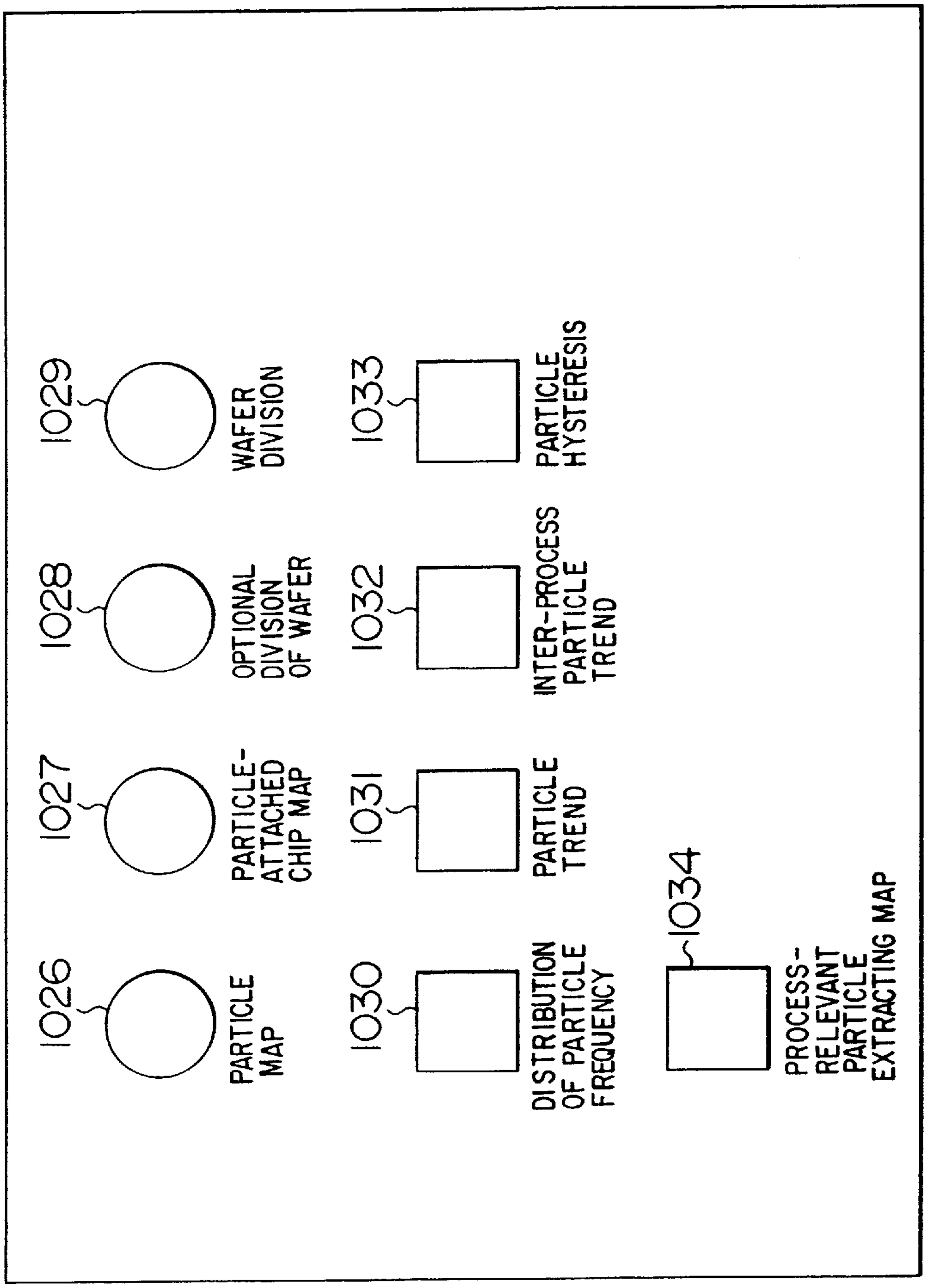
FIG. 11 is a view showing an initial screen.
Figure 12:
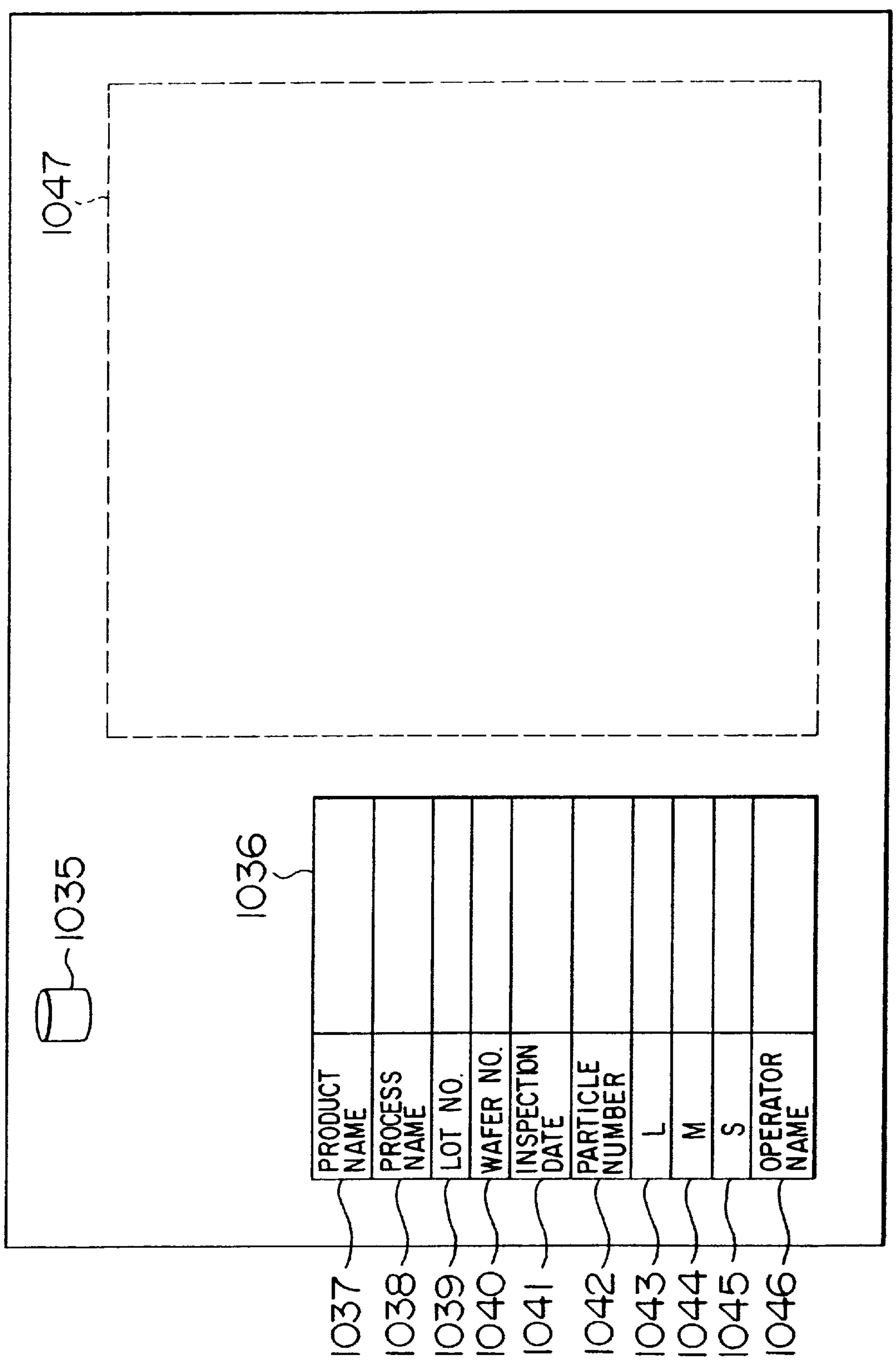
FIG. 12 is a view showing a retrieval screen.
Figure 13:
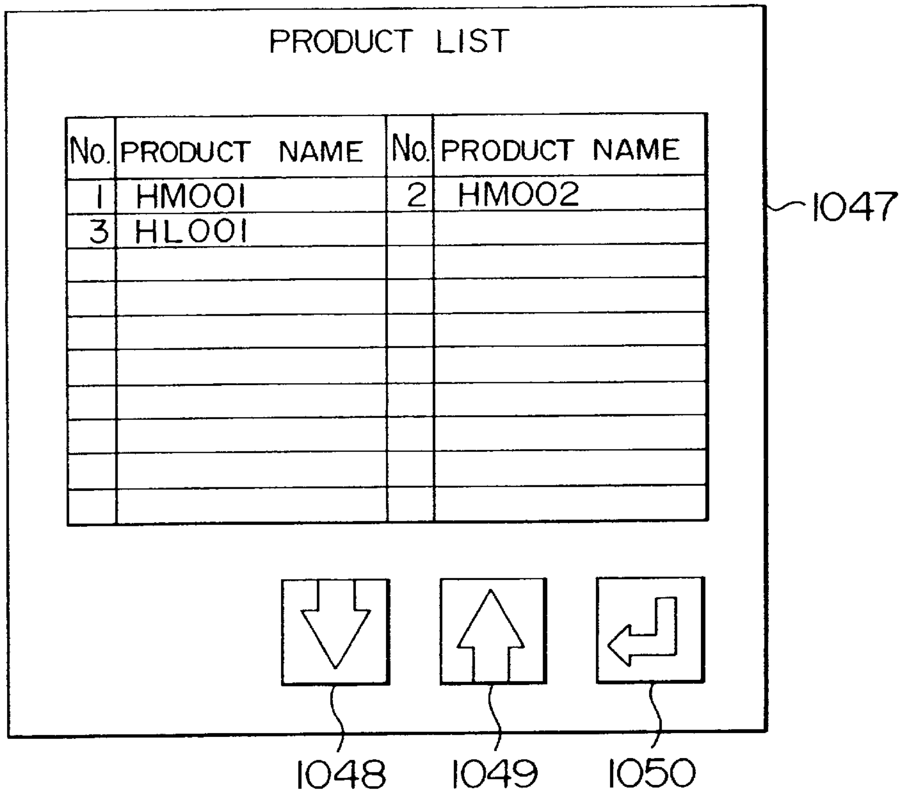
FIGS. 13 to 18 are views respectively showing a list of each data.
Figure 14:
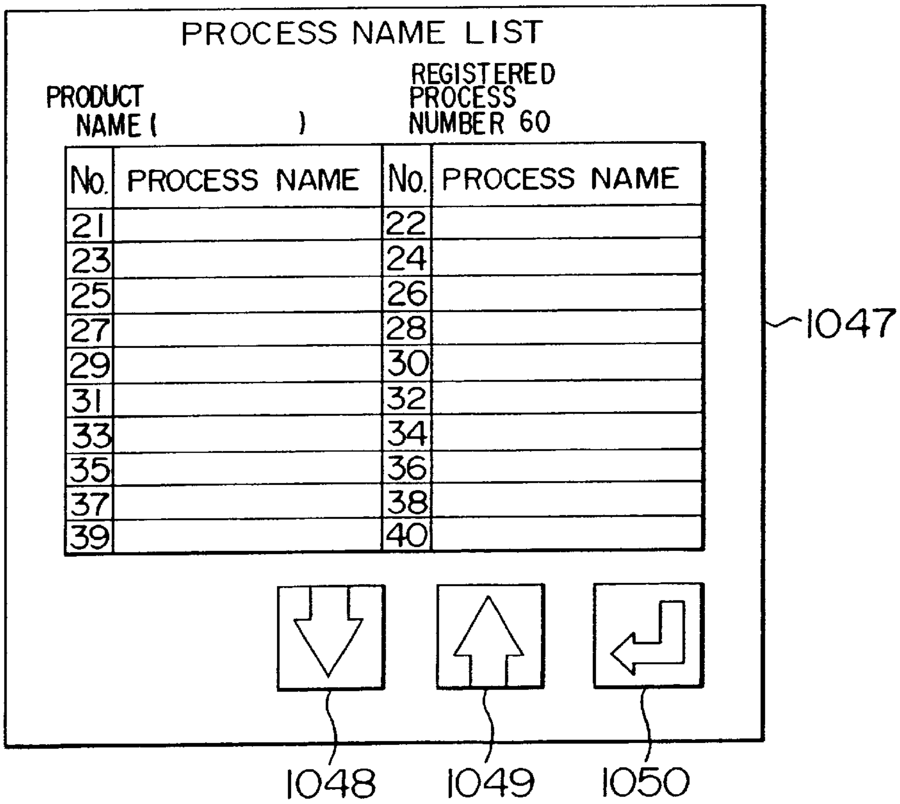
Figure 15:
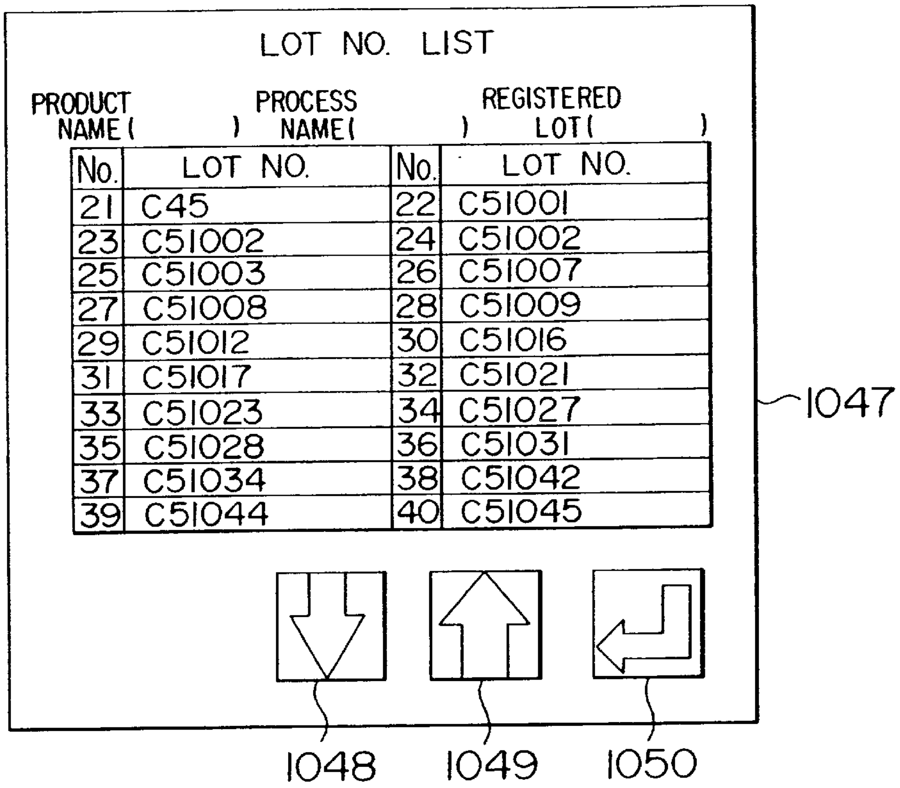
Figure 16:
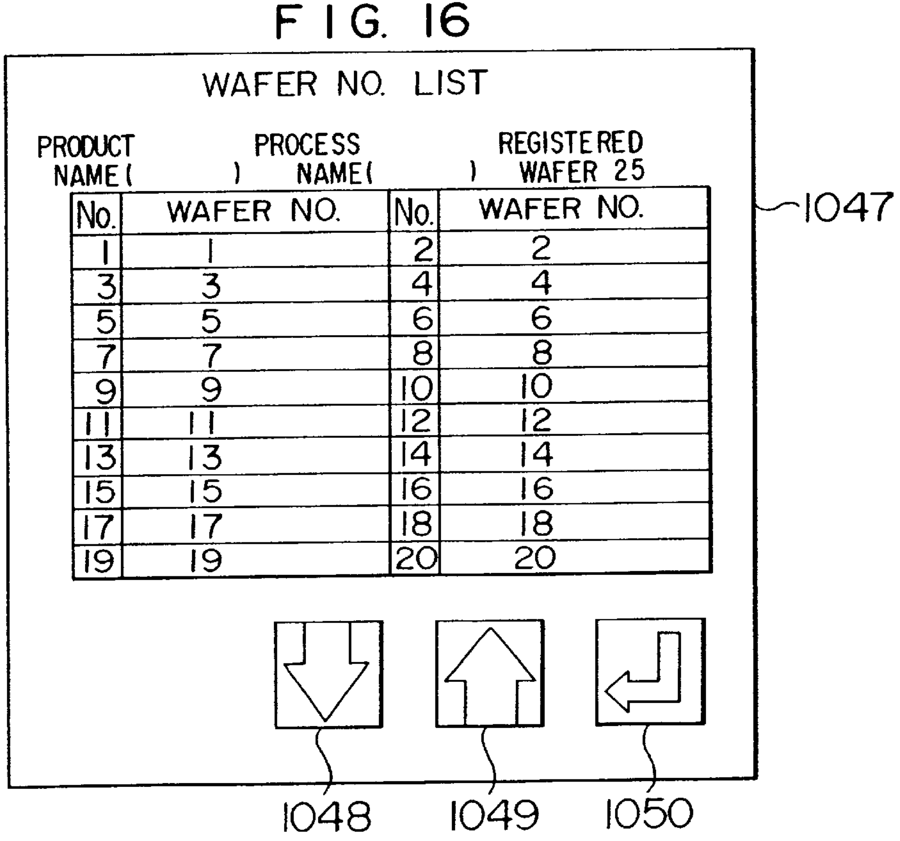
Figure 17:
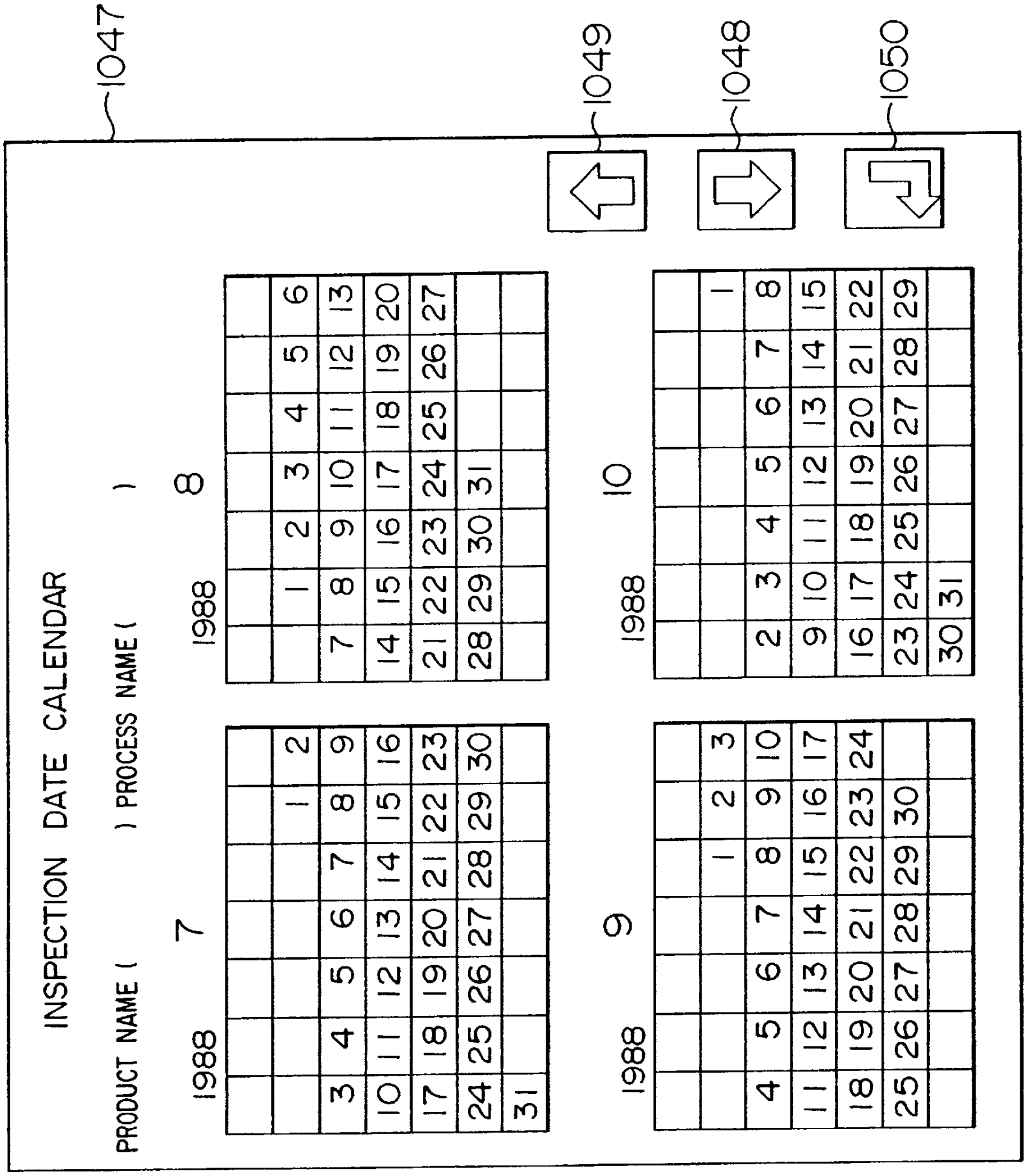
Figure 18:
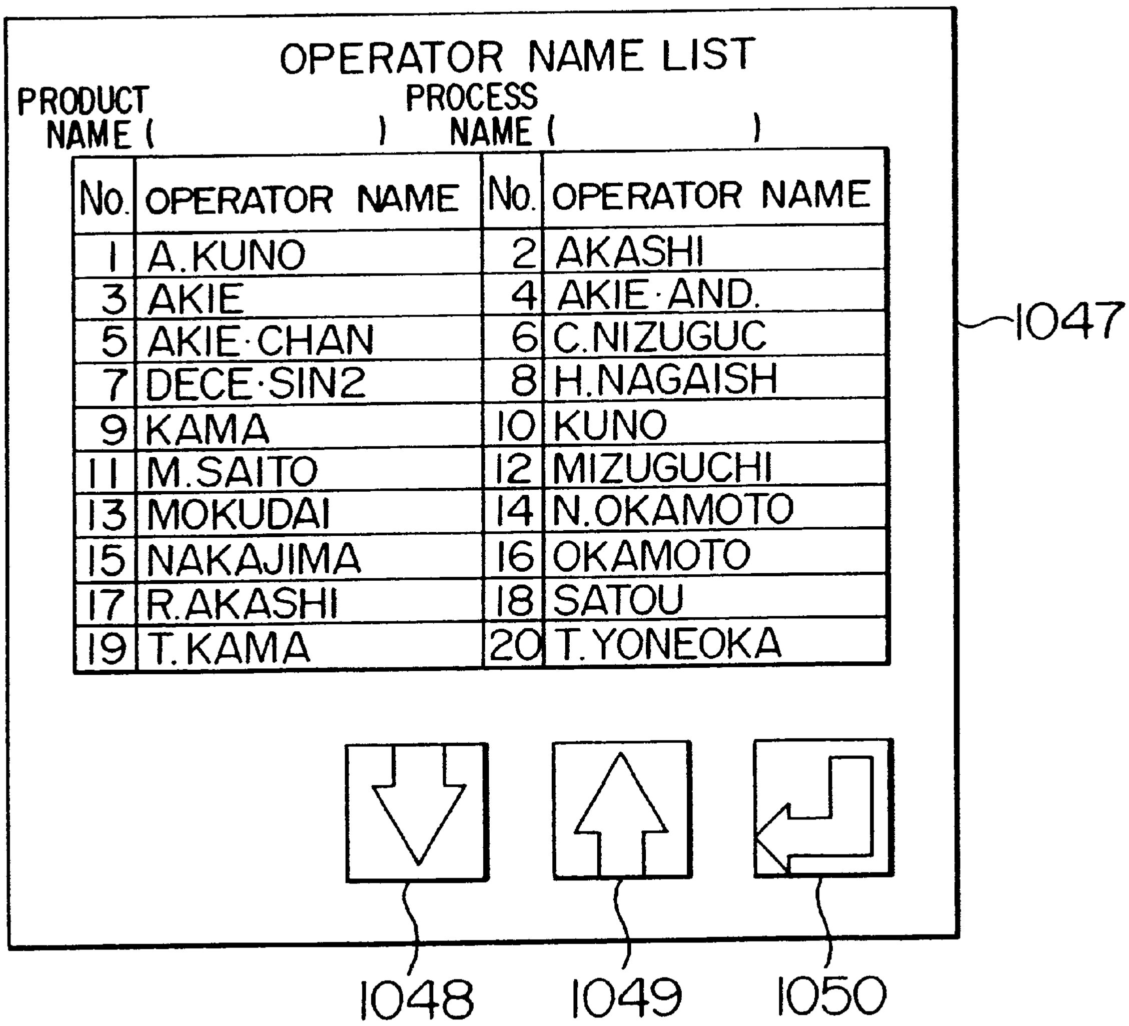

The following description concerns how to use the particle data analysis station 2 described with reference to FIG. 2. In the initial screen shown in FIG. 11, several analysis function icons (1026 to 1034) are displayed. These icons include analysis functions to be described later. An analysis operator selects a desired analysis function icon and then specifies a retrieval condition on a retrieval screen shown in FIG. 12. For specification, one or more items are specified by the mouse 1012 shown in FIG. 4 and then a finish icon 1050 is specified. This retrieval screen comprises a basic data display column 1036 at the lower-left portion of the screen, a database retrieval icon 1036 at the upper-left portion, and a display section 1047 at the central to the right portion, the display section containing a product list, a process list, a lot number list, a wafer number list, an inspection date calendar, and an operator name list. The basic data display column 1036 contains a product name 1037, a process name 1038, a lot number 1039, a wafer number 1040, an inspection date 1041, a particle sum 1042, an L-sized particle number 1043, an M-sized particle number 1044, an S-sized particle number 1045, and an operator name 1046. For specifying the retrieval condition, it is necessary to specify the product name 1037. It is possible to specify the process name 1038, the lot number 1039, the wafer number 1040, the inspection date 1041, and the operator name 1046 if necessary. The specified results are displayed on the basic data display column 1036. By specifying the product name item 1037 on the initial screen using the mouse 1012, the product name list shown in FIG. 13 is displayed on the display section 1047. The displayed list includes all the product names 5001 registered in the database 1010. Further, in FIG. 13, 1048 denotes a lower scroll icon, 1049 denotes an upper scroll icon, and 1050 denotes a finish icon. When the analysis operator specifies one desired product name of the list with the mouse 1012, the specified product name is displayed in the product name item 1037. Next, when the analysis operator specifies the process name in the item 1038 with the mouse 1012, the process name list shown in FIG. 14 is displayed on the display section 1047. This displayed process name list contains only the process name 5002 about the specified product names in the data registered in the database 1010. The analysis operator specifies a desired process name in the process name list with the mouse 1012. Then, when he or she specifies the lot number item 1039 with the mouse 1012, the lot number list is displayed as shown in FIG. 15. This lot number list contains only the lot number 5003 about the specified product name and process name in the data registered in the database 1010. The analysis operator specifies a desired lot number from among the lot number list with the mouse 1012. Then, when the operator specifies the wafer number item 1040 with the mouse 1012, the wafer number list is displayed as shown in FIG. 16. This wafer number list contains only the wafer number 5009 about the product name 50001, the process name 5002, and the lot number 5003, which are all specified, in the data registered in the database 1010. The analysis operator specifies a desired wafer number from among the wafer number list with the mouse 1012. Next, when he or she specifies the inspection date item 1041 with the mouse 1012, an inspection date calendar is displayed as shown in FIG. 17. The inspection date calendar indicates the earliest to the latest month of inspection date 5005 about the product name, the process name, the lot number, and the wafer number, which are all specified, in the data registered in the database 1010. The analysis operator specifies a desired period by specifying the earlier date and the latest date in the inspection date calendar with the mouse 1012. Next, when the operator specifies the operator name item 1046 with the mouse 1012, the operator name list is displayed as shown in FIG. 18. The operator name list contains only the operator names about the product name, the process name, the lot number, the wafer number, and the inspection date, which are all specified, in the data registered in the database 1010. The analysis operator specifies a desired operator name from among the operator name list with the mouse 1012. After the desired item, an analysis operator specifies the database retrieval icon. The particle data analysis station 2 serves to retrieve the satisfactory data about the product name, the process name, the lot number, the wafer number, the inspection date, and the operator name from the particle database 1010 and send it to the particle data processing unit 1009. If no item is specified, the particle data analysis station 2 serves to retrieve all the satisfactory data about the other specified items from the particle database 1010 and send it to the particle data processing unit 1009.

Figure 19:
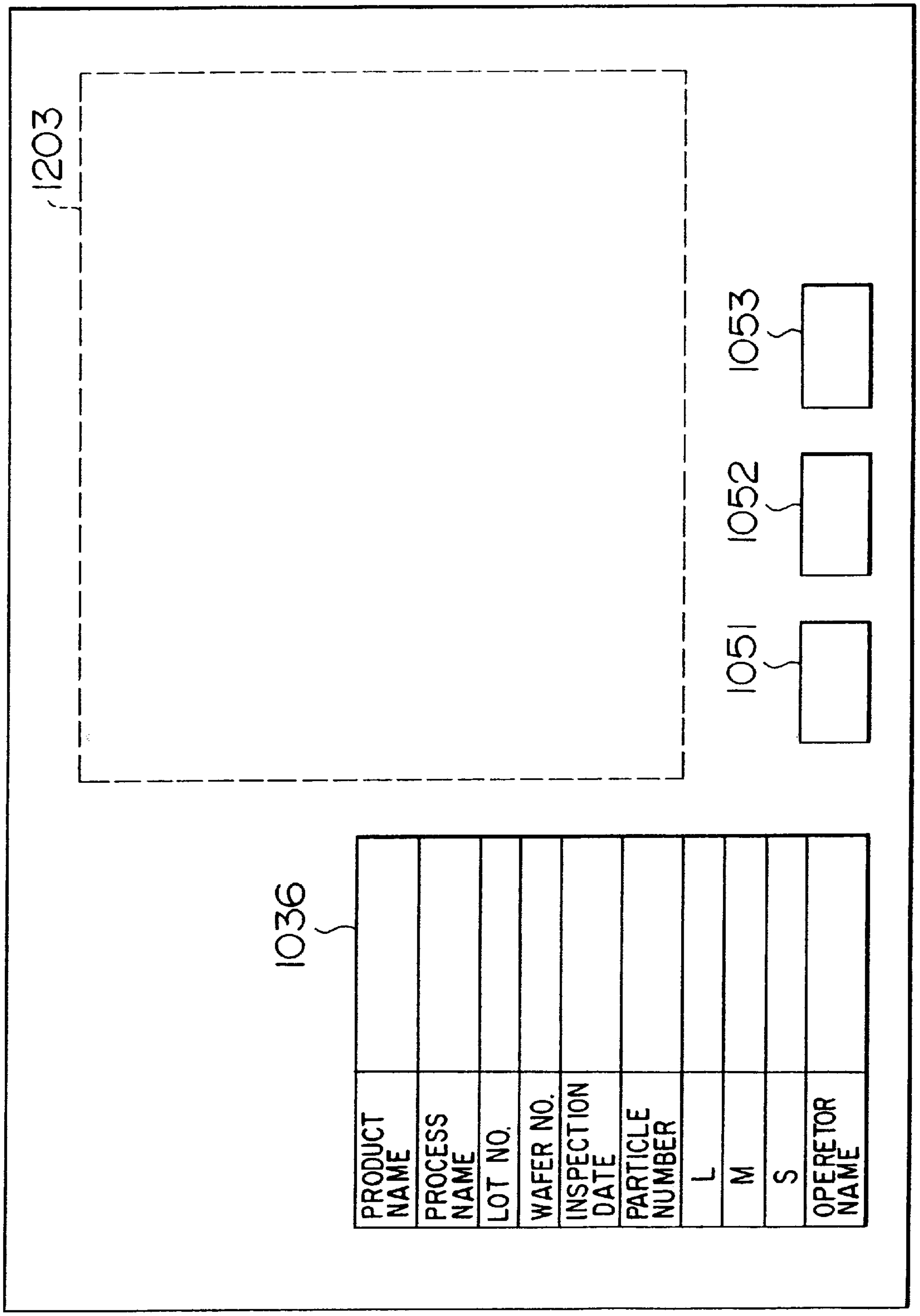
FIG. 19 is a view showing an analysis screen.

When the particle data processing unit 1009 finishes reading of the data, the analysis screen is displayed as shown in FIG. 19. Three operation icons 1051, 1052, 1053 are provided in the lower-central to the lower-right portion of the screen. The basic data display column 1036 is provided in the lower-left portion of the screen. On the central portion is output the analysis result. This basic data display column 1036 on the screen is identical to the basic data display column 1036 on the initial screen shown in FIG. 12. These operation icons serve as a mode change 1051, a hard-copy 1052, and a finish 1053. The mode change icon 1051 is used for changing the analysis mode. The hard-copy icon 1052 is used for printing the screen displayed on the CRT 1013 or the printer 1014. The finish icon 1053 is used for finishing the analysis and returning the screen to the initial screen.

Figure 20:
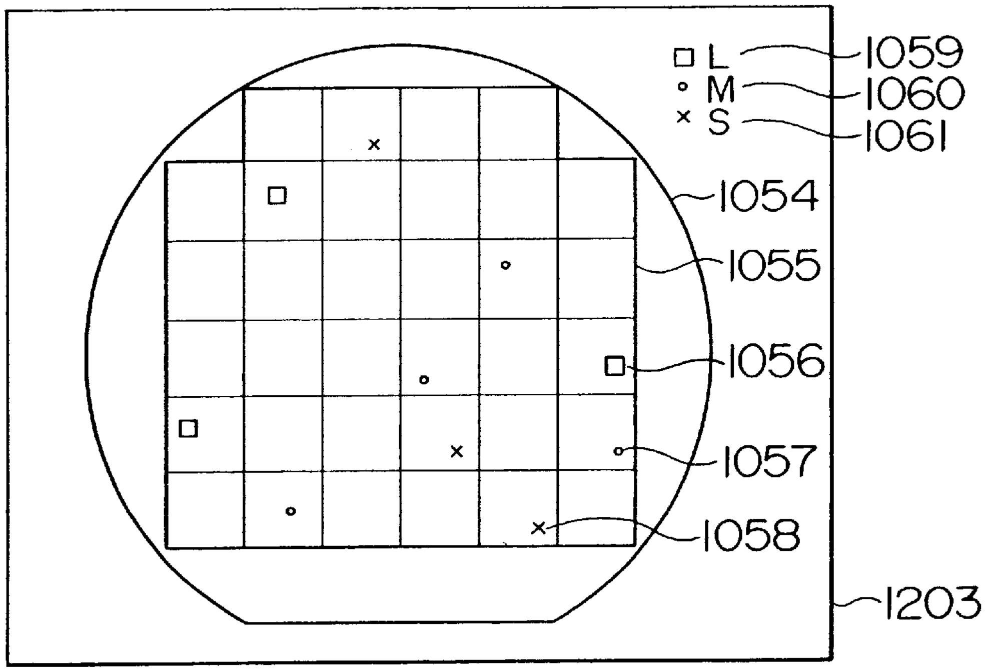
FIG. 20 is a view showing a particle map, used for analyzing the distribution of particles.

Next, the description will be directed to the analysis with reference to FIG. 20, concerning a particle map.

With respect to the present embodiment, how particles are distributed on a wafer is displayed on the basis of the information measured in the particle inspection machine 1.

The analysis operator has to specify a product name. Further, he or she may specify a process name, a lot number, a wafer number, an inspection date, and an operator name if necessary. By specification, the particle database 1010 sends the information about the particle location coordinates and the particle diameters to the memory 1016.

The output depicts an outer circle 1054 of a wafer and indicates particle locations by marks. It may over-depict a border line 1055 of the chip at this time. And, three size kinds of particles 1059, 1060, 1061 have respective display colors or marks. When the mode change icon 1051 is specified, at each specification time, it is possible to selectively represent L-, M-, and S-sized particles. Further, it is also possible to concurrently specify more than one wafer and display all of the particle distributions on the CRT 1013 in an overlapped manner.

Figure 21:
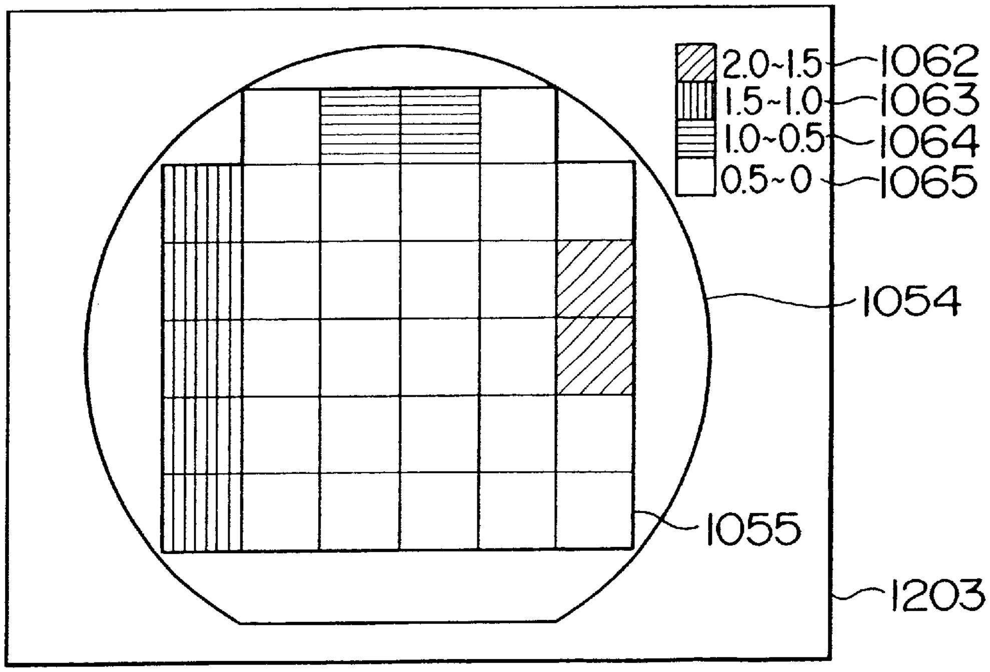
FIG. 21 is a view showing a map about how particles are attached on chips, used for analyzing the distribution of particles.
Figure 22:
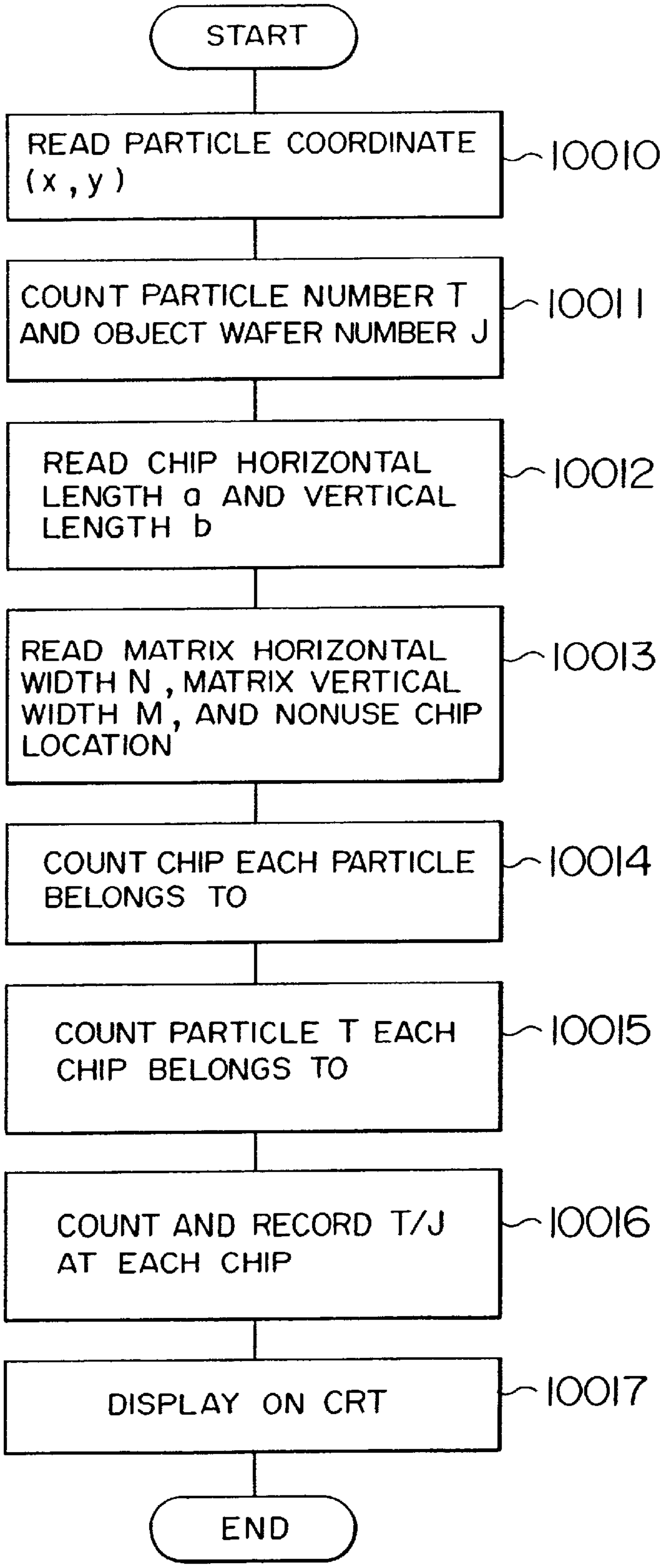
FIG. 22 is a flowchart showing an algorithm for determining which chip particles are attached.

Next, the description will be directed to the analysis with reference to FIGS. 21 and 22. This is referred to as a particle chip map. The particle data processing unit 1009 serves to perform a particle chip determining algorithm shown in FIG. 22 for counting the number of particles existing on each chip. An analysis operator has to specify a product name. And, he or she may specify a process name, a lot number, a wafer number, an inspection date, and an operation name if necessary. By the specification, the location coordinates are retrieved from the particle database 1010 and are stored in the memory 1016 (step 10010). Then, the stored wafer number J is counted (step 10011). And, the chip horizontal width 1020, the chip vertical width 1019 (respectively denoted as a and b), the matrix horizontal width 1023, and the matrix vertical width 1022 are read into the particle data processing unit 1009 from the map information file saved in the internal harddisk 1017. The particle chip determining algorithm will be described later. In the present embodiment, the area of a (n, m)th chip will be represented as;

$$(n-1)a<x<na$$

$$(m-1)b<y<mb$$

where x and y respectively denote an X coordinate and a Y coordinate of each particle. The maximum value of (n, m) is (N, M). For each particle, n and m are calculated as follows (step 10014);

$$n=[x/a]+1$$

$$m=[y/b]+1$$

By the calculation, it is possible to find a chip to which the particles belong. Then, a two-dimensional exponent (n, m) is added to denote the position of each particle. Herein, [z] represents a maximum integer which does not exceed a real number z. For each chip, the particle number is counted (step 10015) for deriving a particle density of each chip per wafer (step 10016). How particles exist on each chip is represented on the CRT 1013 by changing a chip color or meshing a chip according to each number of particles as shown in FIG. 21 (step 10017).

In addition, in FIG. 21, 1062 to 1065 represent the particle number sections per chip.

Next, the description will be directed to how to assist the analysis. This is referred to as the optional division of a wafer.

In the present embodiment, the particle data analysis station 2 serves to divide a wafer to be analyzed on the CRT 1013.

Figure 23:
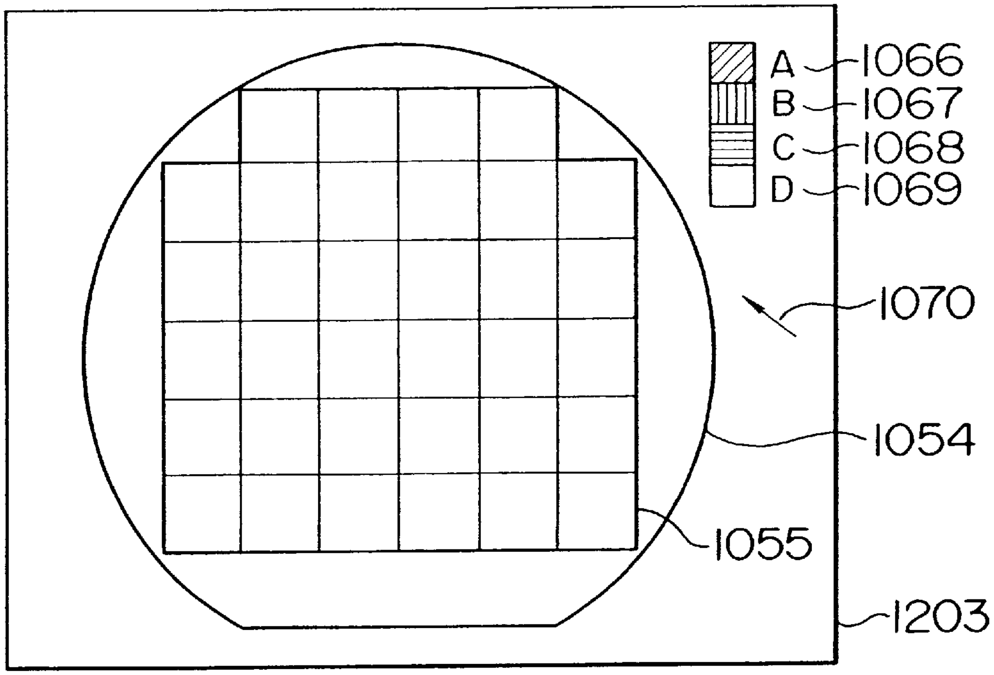
FIG. 23 is a view showing a screen output in case of optionally dividing a wafer, used for analyzing the distribution of particles.
Figure 24:
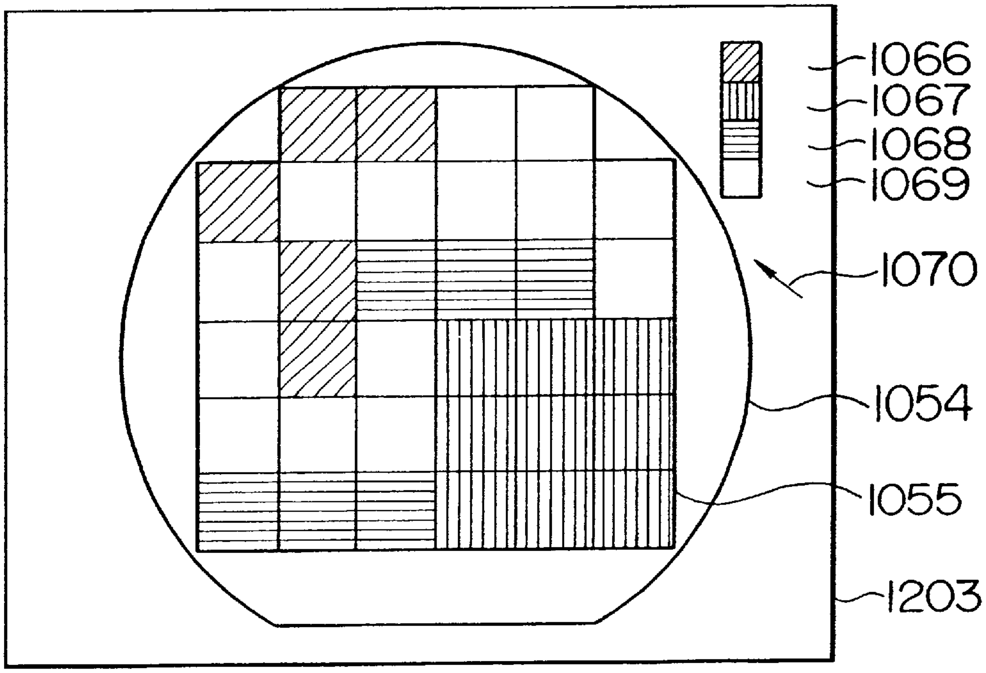
FIG. 24 is a view showing how a wafer is divided, using for analyzing the distribution of particles.

By specifying a product name, it is possible to display a wafer image on which the specified product chips are located on the CRT 1013 in a format shown in FIG. 23. And, an analysis operator specifies one of the area columns 1066 to 1069 on the screen by moving an arrow mark 1070 with the mouse 1012 and then specifies the chip by moving the arrow mark 1070 in order to separate the chips according to each particle density. Once one area of the area columns 1066 to 1069 is specified, the subsequently-specified chips are specified as the area. Each chip is divided by the color or the mesh according to each area. One example of the divided chips is shown in FIG. 24. The divided pattern is recorded as an optional divisional file shown in FIG. 25 in the harddisk 1017 included in the particle data analysis station 2. This recording is done according to each product.

Next, the description will be directed to the analysis with reference to FIG. 26, which relates to wafer division.

The present embodiment is designed to divide a wafer into several areas and to calculate and output a particle density of each area.

In this regard, an analysis operator has to specify a product name and may specify a process name, a lot number, a wafer number, an inspection date, and an operator name if necessary. By the specification, it is possible to save the particle location coordinates 5014, 5015 and the particle size 5016 as shown in FIG. 5C in the internal memory 1016 from the particle database 1010. And, the analysis operator specifies a divisional pattern of a wafer. The divisional pattern can be categorized as a formal divisional pattern, such as a double circle 1083, a triple circle 1082, and a crossed pattern 1084, as shown in FIG. 27, and a pattern created by the wafer optional division specification as described previously. The double circle and the triple circle are respectively created by equally dividing a radius of the wafer regarded as a circle into two or three parts. The crossed division is created by dividing the wafer by the perpendicular bisector of the orientation flat 2000 and a perpendicular passed through the center of the wafer.

The particle data processing unit 1009 derives a particle density of each area from the information about the particle location coordinates and the wafer area division and outputs the result in a graphical format. In the graph shown in FIG. 26, the ordinate 1071 denotes a particle density (number/$cm^2$) and the abscissa 1072 denotes three areas 1073, 1074, 1075 of the triple circle 1082. For obtaining quantitative data, it is possible to represent precise values ($d_1$) 1079, ($d_2$) 1080, and ($d_3$) 1081 at the top of each bar graph. The bar graph may be divided according to the particle sizes S 1076, M 1077, and L 1078 so that the divided sections may have respective colors or meshes. By specifying the mode change icon 1051, each divisional pattern for the analysis can be selected.

Next, the description will be directed to the analysis with reference to FIG. 28, relating to particle number frequency distribution.

The present embodiment is designed to represent the frequency distribution of the number of particles existing on one wafer.

An analysis operator has to specify a product name and a process name and may specify an inspection date, a lot number, and a wafer number if necessary. By the specification, it is possible to save the particle number 5010 shown in FIG. 5B in the external memory 1016 from the particle database 1010.

The particle data processing unit 1009 serves to derive the number of wafers for each range of the specified particle number and output on the screen the result as a histogram. In this graph, the abscissa 1085 denotes the particle number, the maximum value and the divisional range which the analysis operator specifies. The ordinate 1086 denotes the number of wafers.

Next, the description will be directed to an analysis relating to a particle trend chart.

The present embodiment is designed to output how the particle number is changed on time in the process specified by an analysis operator in a graphical manner.

The analysis operator has to specify a product name and a process name and may specify a wafer number, a lot number, an inspection date, and an operator name if necessary. By the specification, it is possible to save the inspection time 5006, the particle number 5010, and the particle size 5016 as shown in FIGS. 5A, 5B and 5C in the memory 1016 from the particle database 1010.

Figure 29:
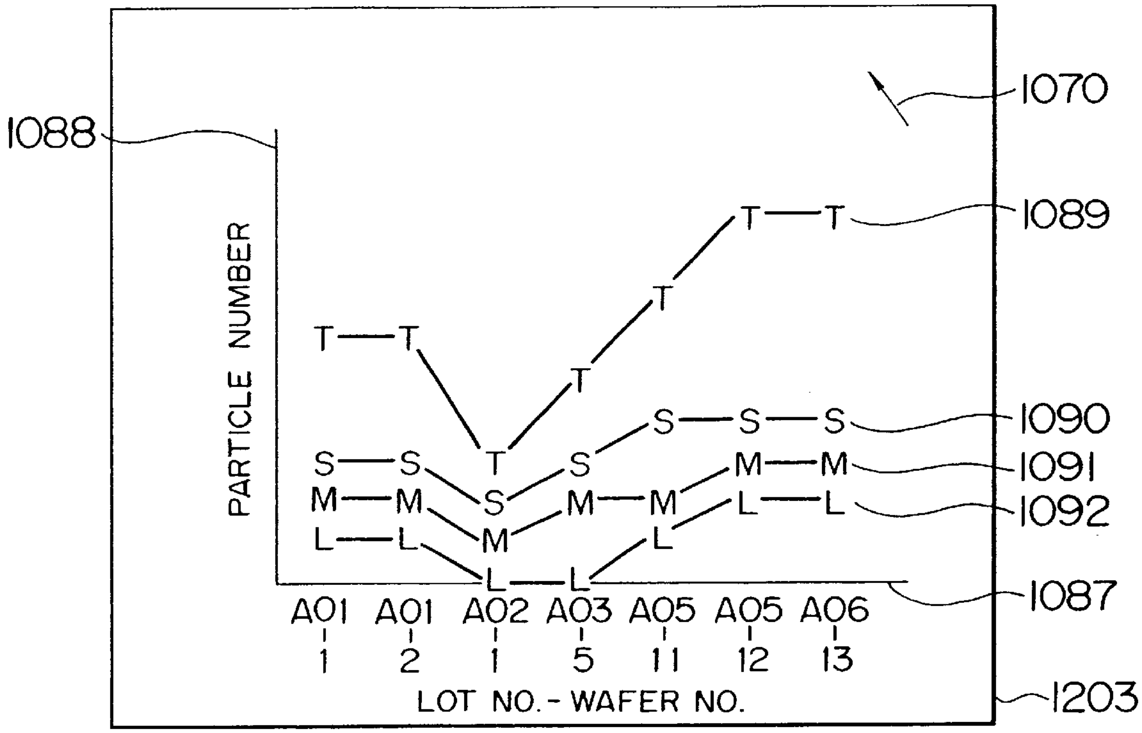
FIG. 29 is a chart showing a particle trend, used for monitoring the amount of particles in number.
Figure 30:
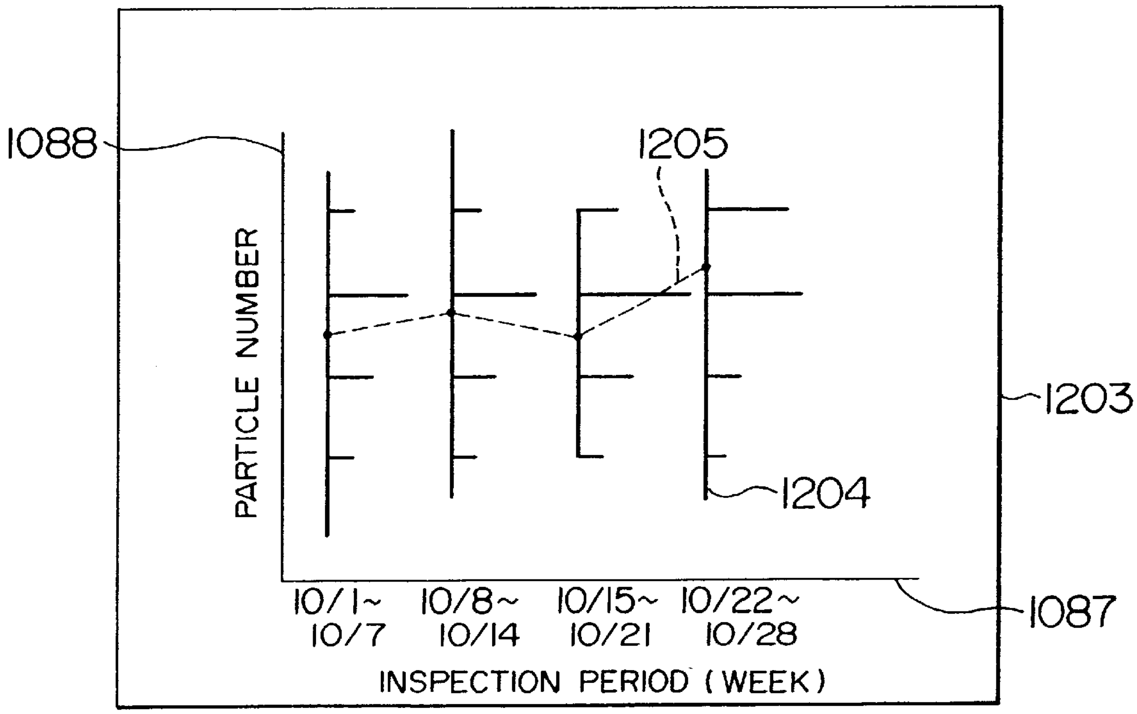
FIG. 30 is a chart showing frequency distributions of particle number in inspection periods and an average trend in each period, used for monitoring the amount of particles in number.

The particle data processing unit 1009 serves to sort the information on time series and output the result in a graphical format. In the graph, the abscissa 1087 denotes a time and the ordinate denotes the particle number. As a unit for the abscissa 1087, it is possible to employ any one of a wafer unit, a lot unit, a date unit, a week unit, and a month unit. In case of a wafer unit, as shown in FIG. 29, the particle data processing unit 1009 outputs a polygon for each of the particle sizes 1090 to 1092. In the polygon, 1089 denotes a total number. In case of a lot unit, a day unit, a week unit, and a month unit, it outputs particle frequency distribution 1204 for each unit in a graphical format shown in FIG. 30. In this graphical manner, it serves to calculate an average value 1205 for each unit and output the result on the frequency distribution 1204 in a polygon manner. The abscissa is allowed to be horizontally scrolled by specifying a right or left half part of the graph with the mouse 1012 if it is impossible to display the information being processed on the screen. The ordinate denotes a range to be selectively specified by the mode change icon 1051.

Figure 31:
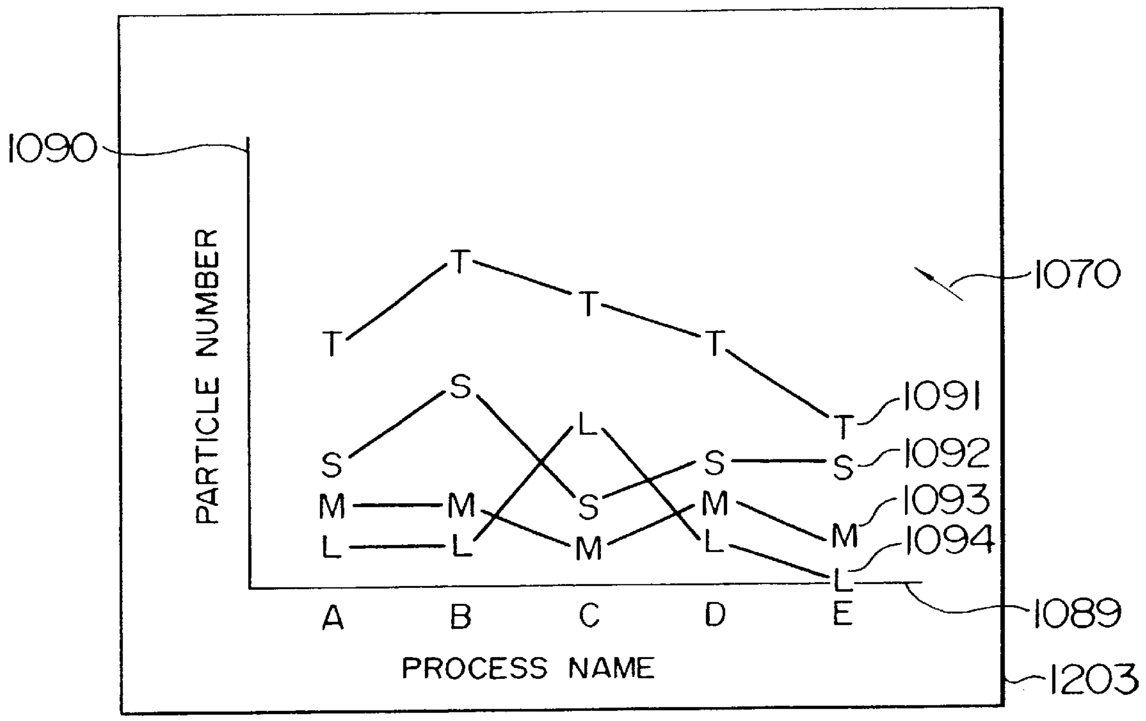
FIG. 31 is a chart showing how the particle number is changed in each sample process, used for monitoring the amount of particles in number.

Next, the description will be directed to an inter-process particle trend with reference to FIG. 31.

The present embodiment is designed to output the particle trend on a wafer between processes in a polygon manner on the basis of the information measured n each process by the particle inspection machine 1.

By specifying more than one process name, it is possible to retrieve the information about the number of all particles 5010 for each wafer, the particle size 5016, and the inspection date and time 5005, 5006 from the particle database 1010 and save the retrieved information in the internal memory 1016.

The particle data processing unit 1009 serves to count the number of particles for each particle size, sort the process names in the inspection order given when the process name is specified, and output the particle number on the CRT 1013 as a polygon. In the polygon, it is possible to change lines and dots for each of the particle sizes (1092 to 1094) for displaying these size kinds of particles at the time of or separately from the number of all particles (1091). The abscissa 1089 denotes the sequence of processes (inspection time series) and has fixed intervals. The ordinate denotes an average particle number per wafer. If there exist so many specified processes that all of them are not displayed on the screen, it is possible to scroll the axis horizontally with the method described previously with respect to the analysis of particle trend.

Figure 32:
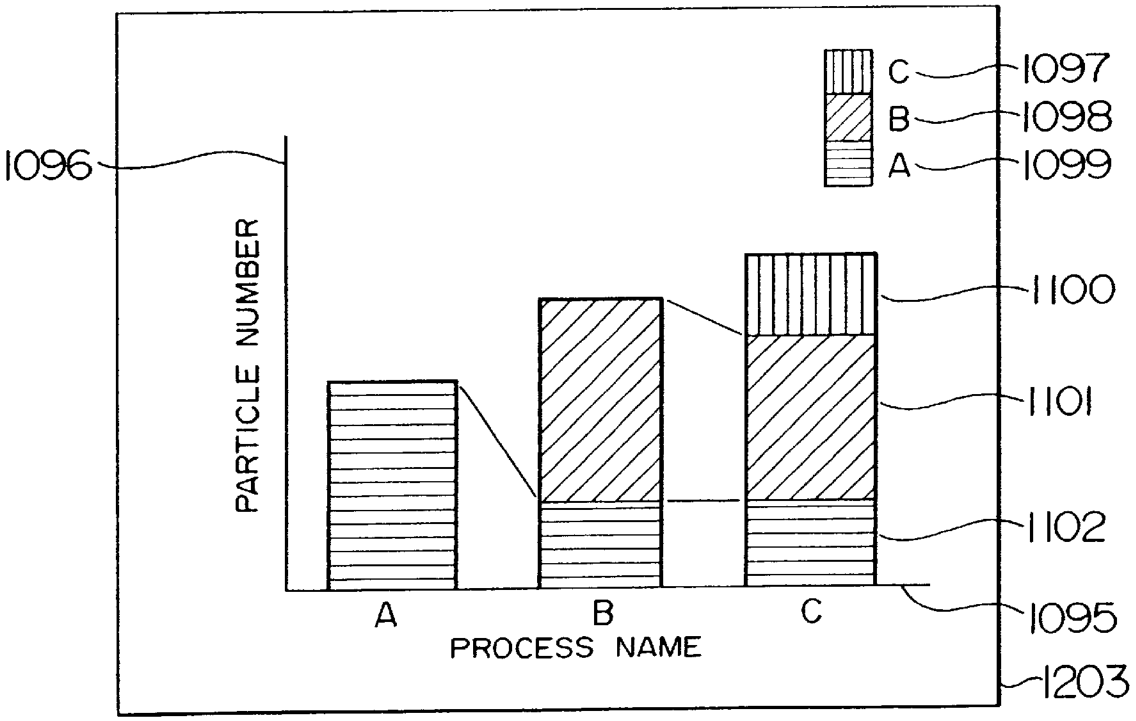
FIG. 32 is a chart showing the particle hysteresis, which information is used for finding a critical process.

Next, the description will be directed to particle hysteresis with reference to FIG. 32.

The present embodiment is designed to output how the particles are attached or removed in each process in a graphical manner.

An analysis operator has to specify a product name, more than one process name, and a lot number and may specify a wafer number if necessary. By the specification, it is possible to save the particle location coordinates 5014, 5015 on the specified wafer, the inspection date 5005, and the inspection time 5006 as shown in FIG. 5 in the memory 1016 from the particle database 1010.

Figures 33, 34:
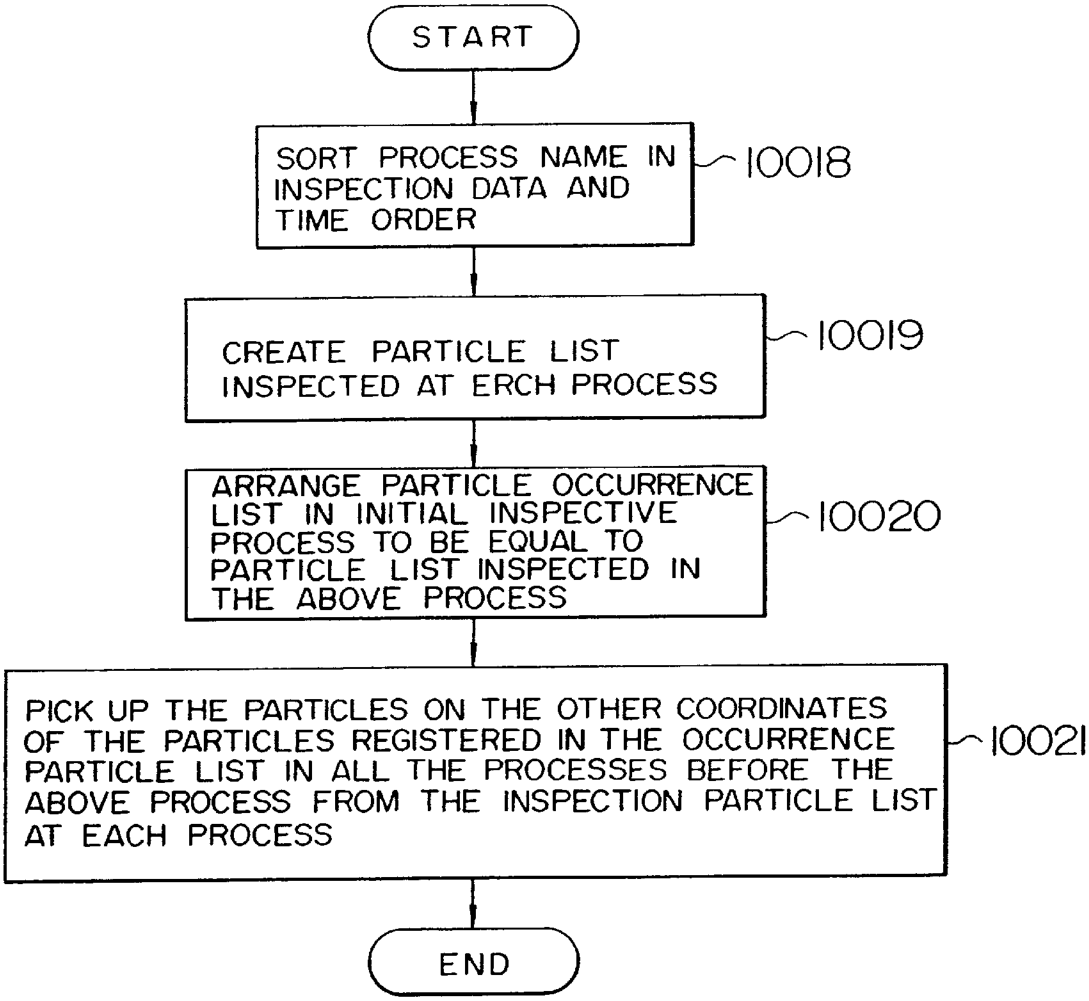
FIG. 33 is a flowchart showing an algorithm for particle trace.
FIG. 34 is a chart showing a format containing an inspected particle list and an existing particle list.

In the particle data processing unit 1009, the particle trace algorithm to be described later clearly indicates how the particles are attached or removed in each process. The particle trace algorithm will be described in FIG. 33. At first, the algorithm sorts the specified process names in earlier order by referencing the inspection date 5005 and the inspection time 5006 (step 10018). Then, it creates a sensed particle list for each process (step 10019) and then makes the caused particle list in the initial process identical to the sensed particle list therein (step 10020). The format of the sensed particle list is equal to that of the caused particle list, which is shown in FIG. 34. Next, the algorithm calculates a distance between the particle location coordinates on the wafer in the initial process and the particle location coordinates on the same wafer in the next process in the recording order of the coordinate data. If a calculated distance is smaller than a predetermined constant value R, these two particles about the distance are specified as the same. Then, the similar calculation is done about the next particle. If no particles in the second process are found to be equal to the particles sensed in the initial process, it is determined that the particles are removed. If no particles sensed in a process are found to be equal to the particles sensed in the previous process, it is determined that the particles are newly attached in the process. The particles to be newly attached in the new process are registered in the particle occurrence list in the new process (step 10021). The similar calculation is done in the order of the earlier processes.

As shown in FIG. 32, the particle data processing unit 1009 serves to output a bar chart in which the ordinate 1096 denotes a particle number and the abscissa 1095 denotes a process name. The process name is ranged from the left side in the earlier order. In the bar chart, the attached particles are separated in a layered manner in each process A, B or C (three layers 1100, 1101, 1102 shown in FIG. 32). These layers are respectively represented by colors and meshes and the line is drawn between the upper and the lower lines of one layer and those of another layer. If two or more wafers are specified, the process tracing is done for each wafer. What is displayed on one screen is an average value of these wafers.

Next, the description will be directed to a process unit particle map.

The present embodiment is designed to extract only the particles attached on the wafer in the same process on the basis of the information measured by the particle inspection machine 1 in each process and then output the result as a particle map shown in FIG. 20.

An analysis operator has to specify a product name, two or more process names, and a lot number and may specify a wafer number if necessary. By the specification, the location coordinates 5014, 5015, the inspection date and time 5005, 5006, and the process name are saved in the internal memory 1016 from the database 1010.

The particle data processing unit 1009 serves to create the particle occurrence list in each process using the particle trace algorithm described previously. After finishing the procedure, the process unit particle map is displayed in the inspection process order. For displaying the next step, it is necessary to specify the mode change icon 1051.

Figure 35:
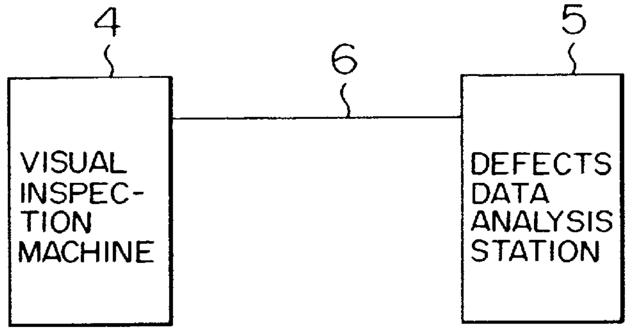
FIG. 35 is a view showing partial arrangement of the visual inspection system shown in FIG. 1.

With reference to FIG. 35, the visual inspection machine 4 and the defects data analysis station 5 in the inspection data analysis system mentioned with reference to FIG. 1 are detailed. The present system comprises the visual inspection machine 4 and the defects data analysis station 5 for analyzing the data supplied from the visual inspection machine 4. The visual inspection machine is connected to the defects data analysis station 5 through the communication line 6.

Figure 36:
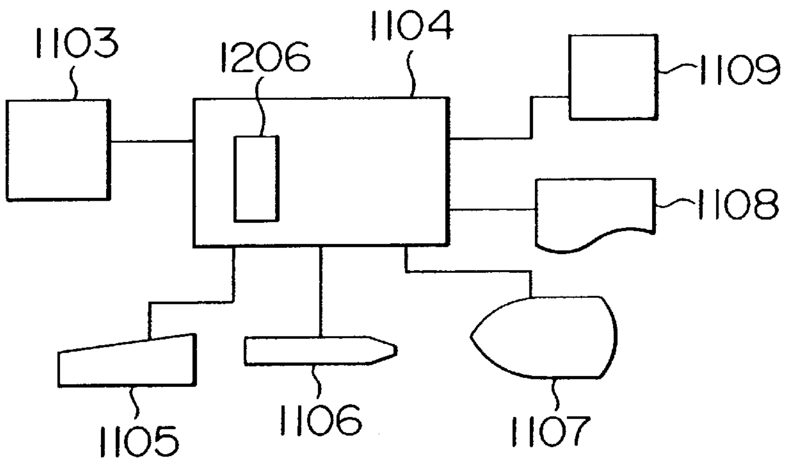
FIG. 36 is a view showing arrangement of the visual inspection machine shown in FIG. 35.

FIG. 36 illustrates the arrangement of the visual inspection machine 4, which comprises a defects sensing section 1103 for sensing particles and pattern defects generally referred to as defects, a defects sensing signal processing unit 1104, a memory 1206, a keyboard 1105, a bar-code reader 1106, both of which serve as input units, a CRT 1107, a printer 1108, both of which serve as output units, and an external communication section 1109 which serve to communicate with the defects data analysis station 5. The visual inspection machine 4 provides functions of recognizing two-dimensional coordinates, sizes, and kinds of the visual sensed defects on a wafer and counting the number of defects on the wafer, the number of critical defects, the number of critical defects in the inspected process, the number of chips with defects, the number of chips with critical defects, the number of chips with critical defects in the process, and the number of inspection chips. The kind and critical level of the defects are determined by the analysis operator observing a defects image displayed on the CRT 1107. And, if the analysis operator determines that the observed defects are critical and caused in the inspected process, these defects are categorized as the critical defects in the inspected process.

Figure 37:
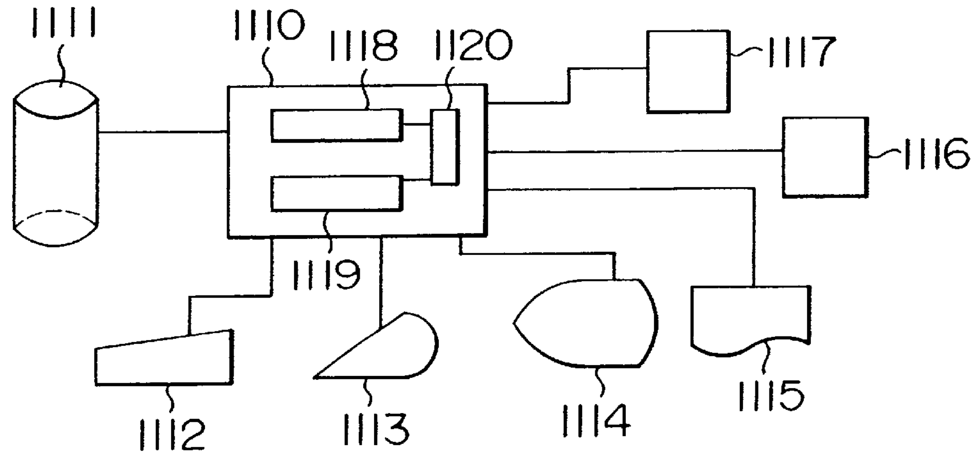
FIG. 37 is a view showing arrangement of the defects data analysis station shown in FIG. 35.

FIG. 37 illustrates the arrangement of the defects data analysis station 5, which comprises a defects data processing unit 1110, a defects database 1111, a keyboard 1112, a mouse 1113, both of which serve as input units, a CRT 1114, a printer 1115, both of which serve as output units, an external communication section 1116 serving to communicate with the visual inspection machine 4, a floppy disk drive 1117, a memory 1118 contained in the defects data processing unit, a harddisk 1119, and a CPU 1120.

The visual inspection machine 4 receives the defects management data such as a type of a wafer to be inspected, a process name to be inspected, a lot number, a wafer number, an inspection data and time, and an operator name, which are inputted by the keyboard 1105 or the bar-code reader 1106. The memory 1206 serves to save both of the defects inspection data and the defects management data. The defects inspection data contains the number of defects on an inspected wafer, the number of critical defects, the number of critical defects in the inspected process, the number of chips with defects, the number of chips with critical defects, the number of chips with critical defects in the inspected process, the location coordinates of defects inside of the inspected chip, and the type and the critical level of the defects.

The arrangement of the defects database 1111 will be described with reference to FIG. 38. The basic arrangement is the same as that of the particle database 1010 described previously.

Figures 39, 40:
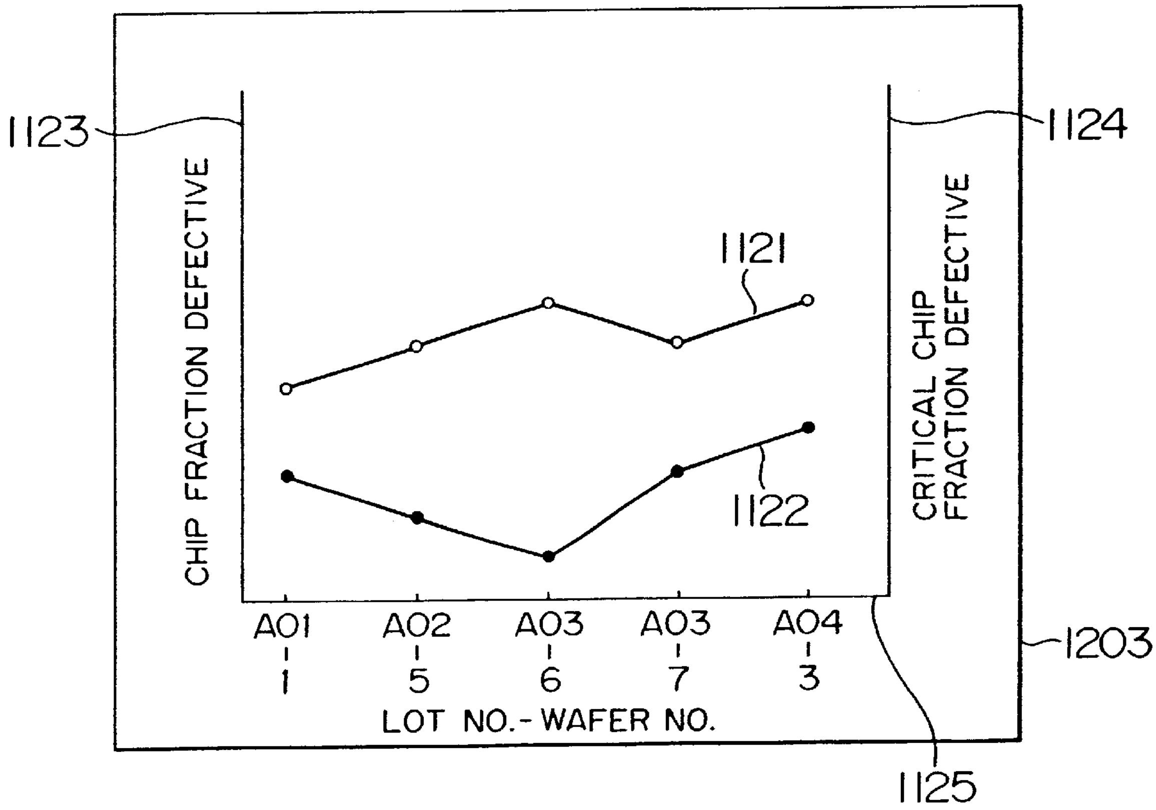
FIG. 39 is a chart showing a wafer number management file for each product.
FIG. 40 is a chart showing how a chip fraction defective is changed.

The particle defects data processing unit 1110 includes a product unit wafer number management file shown in FIG. 39, the map information file described previously, and the harddisk 1119.

Next, the flow of data will be described in the present system. After the visual inspection machine 4 finishes the inspection of one wafer, it sends the defects management data and the defects inspection data to the defects data analysis station 5 through the communication line 6. The subsequent flow is substantially same as the flow of data described in the embodiment 2, except that the processing data is the defects management data and the defects inspection data and is processed on a wafer unit.

A description of how to use the defects data analysis station 5 will be provided. It is generally the same as the description about how to use the particle data analysis station 2. The different respect is that the basic data column 1036 displays the number of critical defects, a fraction defective, and a defect density in place of the number of l-sized particles, the number of M-sized particles, and the number of S-sized particles and the analysis function icon indicates analysis functions described previously.

Next, the description will be directed to an analysis relating to a defect map.

This operation is generally the same as that designed to analyze particles using the particle inspection system, while the present operation is designed to analyze defects using the visual inspection system described previously. In the output form, the particle sizes have been represented by the colors or marks on the dots, while the present embodiment represents the categories of defects by the colors or marks.

Next, the description will be directed to the analysis relating to a defect chip map.

The present operation is generally the same as that designed to analyze particles using the particle inspection system, while the present operation is designed to analyze defects using the visual inspection system.

Next, the description will be directed to analysis relating to wafer division.

The present operation is generally the same as that designed to analyze particles using the particle inspection system, while the present operation is designed to analyze the defects using the visual inspection system.

Next, the description will be directed to analysis relating to defect number frequency distribution.

The present operation is generally the same as that designed to analyze the particles using the particle inspection system, while the present operation is designed to analyze the defects using the visual inspection system.

Next, the description will be directed to an analysis of defect trend.

The present operation is generally the same as that designed to analyze the particles using the particle inspection system, while the present operation is designed to analyze the defects using the visual inspection system. In the output form, the particle sizes have been represented by the colors or marks on the polygonal lines and dots, while the present operation represents the categories of defects by them.

Next, the description will be directed to an analysis of inter-process defect trend.

The present operation is generally the same as that designed to analyze the particles using the particle inspection system, while the present operation is designed to analyze the defects using the visual inspection system. In the output format, the arrangement discussed regarding FIG. 29 represents particle sizes, while the present operation represents the categories of the defects, by the colors or marks on the polygon lines and the dots, respectively.

Next, the description will be directed to analysis of defect hysteresis.

The present operation is generally the same as that designed to analyze the particles using the particle inspection system, while the present operation is designed to analyze the defects using the visual inspection system.

Next, the description will be directed to the analysis with reference to FIG. 40. This operation is referred to as chip fraction defective trend. An analysis operator has to specify a product name, a process name, and an inspection date and may specify a lot number if necessary. By the specification, it is possible to save a lot number in the specified lot, a wafer number, a visual defect chip number 5045, a critical defect chip number 5044, an inspection chip number, an inspection time 5039 in the memory 1118 from the defects database 1111. The defect data processing unit serves to calculate the chip fraction defective and the critical chip fraction defective on the basis of the foregoing data in accordance with the following equations;

chip fraction defective=defects chip number/inspected chip number×100 critical chip fraction defective=critical defects chip number/inspected chip number×100

The data about each wafer is sorted in time sequence order on the basis of the inspection date 5038 and the inspection time 5039.

On the CRT 1114 as an output form, the trends of the chip fraction defective 1112 and the critical chip fraction defective 1122 are displayed as polygons having respective colors or polygon types. In the polygon, the left-hand ordinate 1124 denotes the chip fraction defective, the right-hand ordinate 1125 denotes the critical chip fraction defective, and the abscissa denotes the lot number and wafer number, which are displayed in the earlier order from the left hand.

Next, the description will be directed to analysis relating to chip defect density trend. An analysis operator has to specify a product name, a process name, and an inspection date and may specify a lot number if necessary. By the specification, it is possible to save a lot number and a wafer number in the inspected lot, a defects number 5043, an inspected chip number, and an inspection time 5039 in internal memory 1118 from the defects database 1111. The defects data processing unit 1110 serves to calculate a chip defects density and a critical chip defects density on the basis of the saved data in accordance with the following equations;

chip defects density=critical defects number/inspected chip number×100 critical chip defects density=critical defects number/inspected chip number×100

And, the data about each wafer is sorted in time sequence order on the basis of the inspection date 5038 and the inspection time 5039.

Figure 41:
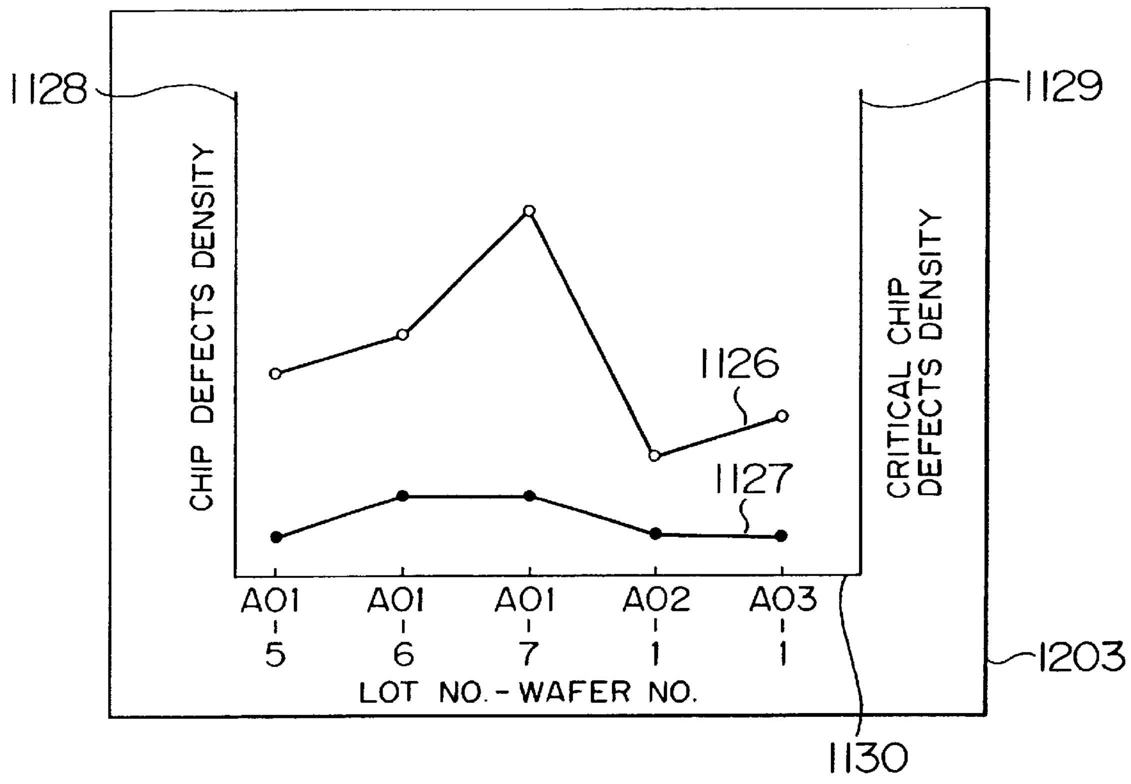
FIG. 41 is a chart showing how a chip defects density is changed.
Figure 42:
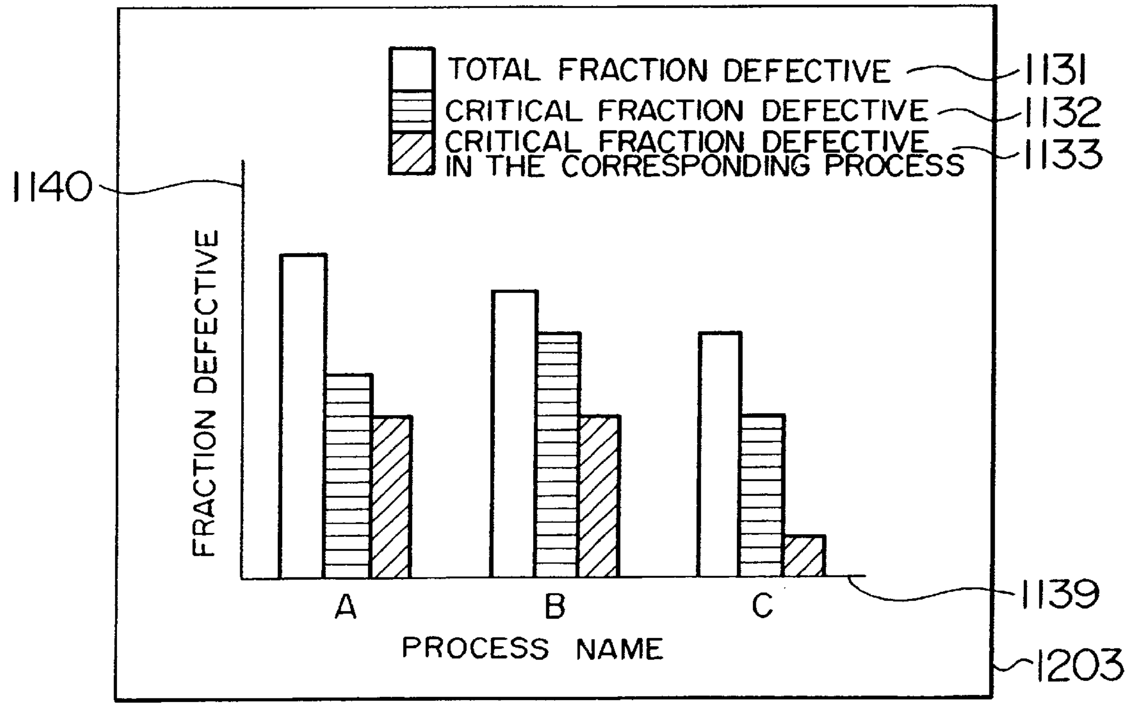
FIG. 42 is a chart showing a fraction defective in each sample process.

On the CRT 1114 as an output form, the trends about the chip defects density and the critical chip defects density are displayed by polygons 1126 and 1127 having respective colors or polygon types. The lefthand ordinate 1128 denotes a chip defects density, the right-hand ordinate 1129 denotes a critical chip defects density, and the abscissa denotes a lot number and a wafer number, which are displayed in earlier order from the left hand side of FIG. 41.

Next, the description will be directed to an analysis referred to as a process unit fraction defective.

An analysis operator has to specify a product name and two or more process names and may specify a lot number, a wafer number, and an inspection date if necessary. By the specification, it is possible to save the corresponding lot and wafer numbers, a defective chip sum, a critical defective chip sum, a critical defective chip sum and an inspected chip number in the inspected process, an inspection date, and an inspection time in the internal memory 1118 from the defects database 1111. On the basis of the data, the defects data processing unit serves to calculate a total fraction defective 1131, a critical fraction defective 1132, and an inspected-process critical fraction defective 1133 in accordance with the following equations.

total fraction defective=defective chip sum/inspected chip sum×100 critical fraction defective=critical defective chip sum/inspected chip sum×100 inspected-process fraction defective=inspected-process critical defective chip sum/inspected chip sum×100 wherein if there exists data about two or more wafers in a process, the data is averaged about the wafers. The product names are sorted in earlier order on the basis of the inspection date 5038 and the inspection time 5039.

On the CRT 1114 as an output form, it is possible to display, in each process, the total fraction defective 1131, the critical fraction defective 1132, and the inspected-process critical fraction defective 1133 using polygons. In the polygons, the abscissa 1139 denotes the processes, which are ranged in earlier order and the ordinate 1140 denotes the fraction defectives having respective colors and meshes.

Figure 43:
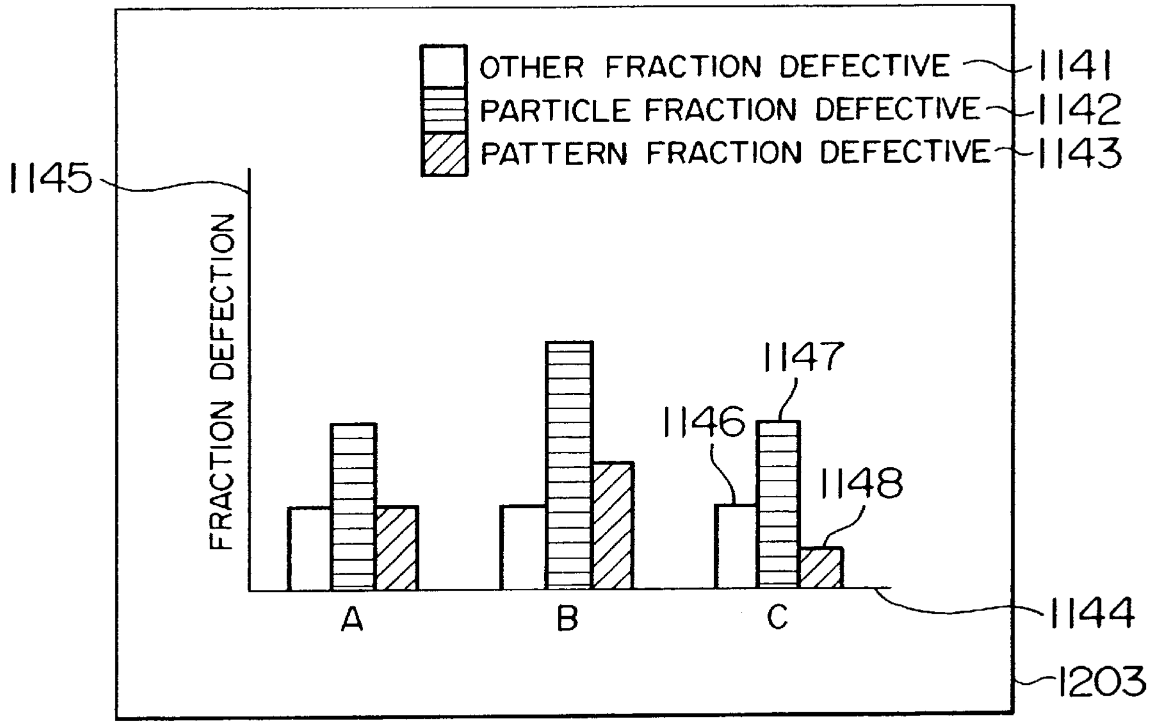
FIG. 43 is a chart showing another fraction defective in each sample process.

Next, the description will be directed to an analysis method of a process unit fraction defective with reference to FIG. 43. An analysis operator has to specify a product name and two or more process names and may specify a lot number, a wafer number, and an inspection date if necessary. By the specification, it is possible to save the corresponding lot and wafer numbers, a pattern defect chip number, a particle-defect chip number, the other type defect chip number, an inspected chip number, an inspection date, and an inspection time in the internal memory 1118 from the defects database 1111. On the basis of the data, the defects data processing unit serves to calculate a fraction defective of the pattern-defect chip, a fraction defective of the particle-defect chip, and a fraction defective of the other type-defect chip in accordance with the following equations;

fraction defective of the pattern-defect chip=pattern-defect chip number/inspected chip number×100 fraction defective of the particle-defect chip=particle-defect chip number/inspected chip number×100 fraction defective of the other type-defect chip=the other type-defect chip number/inspected chip number×100 wherein if there exists data about two or more wafers in a process, the data is averaged about the wafers. The process names are ranged in time sequence order on the basis of the inspection date and the inspection time.

On the CRT 1114 as an output form, it is possible to display, for each process, the pattern-defect chip fraction defective 1143, the particle-defect chip fraction defective 1142, and the other type-defect chip fraction defective 1141 using polygons 1148, 1147, 1146. In the polygons, the axis of abscissa 1143 denotes the processes, which are arranged in time sequence order from the left hand side of FIG. 43, and the ordinate denotes the pattern fractions defective having respective colors or meshes.

Figure 44:
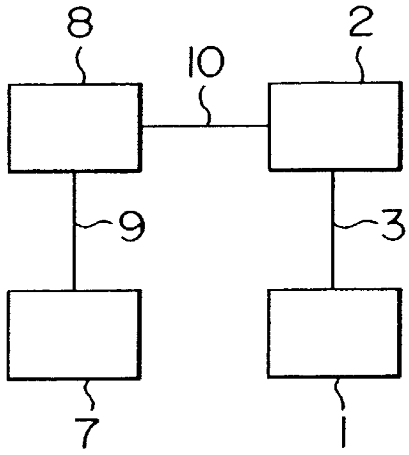
FIG. 44 is a diagram showing a particle inspection machine, a particle data analysis station, a probing tester, and a probing test data analysis station, which correspond to partial arrangement of the system shown in FIG. 1.

An embodiment having the particle inspection machine 1, the particle data analysis station 2, the probing tester 7, and the probing test data analysis station 8 is illustrated in FIG. 44.

Figure 45:
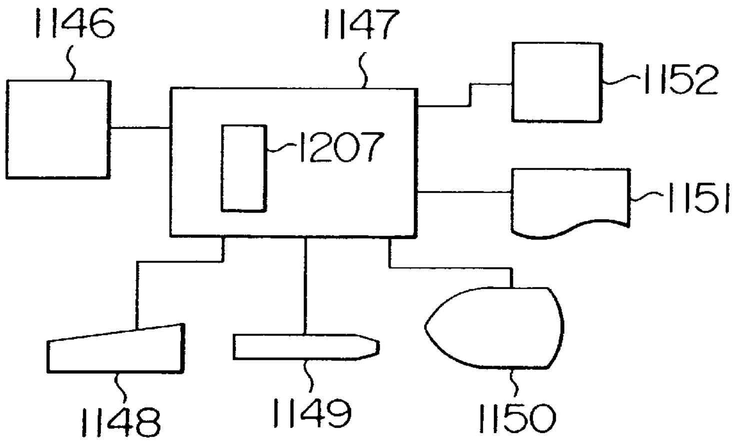
FIG. 45 is a diagram showing arrangement of the probing tester.

FIG. 45 illustrates the arrangement of the probing tester 7, which comprises a probing test unit 1146, a probing data inspection and processing unit 1147, a keyboard 1148, a bar-code reader 1149, both of which are served as an input unit, a CRT 1150, a printer 1151, both of which are served as an output unit, an external communication unit 1152 for communicating with the probing test data analysis station 8, and a memory 1207 contained in the data processing unit 1147. This probing tester 7 serves to test a product character of semiconductor devices integrated on a wafer.

Figure 46:
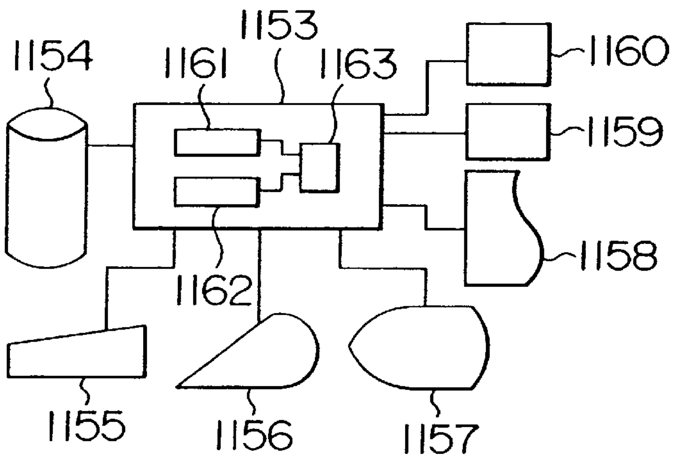
FIG. 46 is a diagram showing arrangement of the probing data analysis station.

FIG. 46 illustrates the arrangement of the probing test data analysis station 8, which comprises a probing data processing unit 1153, a probing database 1154 for saving the result supplied by the probing data processing unit 1153, a keyboard 1155, a mouse 1156, both of which are served as an input unit, a CRT 1157, a printer 1158, both of which are served as an output unit, a first external communication unit 1159 for communicating with the probing tester 7, a second external communication unit 1160 for communicating with the particle data analysis station 2, a memory 1161, a harddisk 1162, and a CPU 1163. The arrangement of the particle data analysis station 2 shown in FIG. 44 is generally same as that shown in FIG. 4, except that it additionally provides an external communication unit 1164 for communicating with the probing data inspection analysis station 8 (see FIG. 47).

Figure 6:
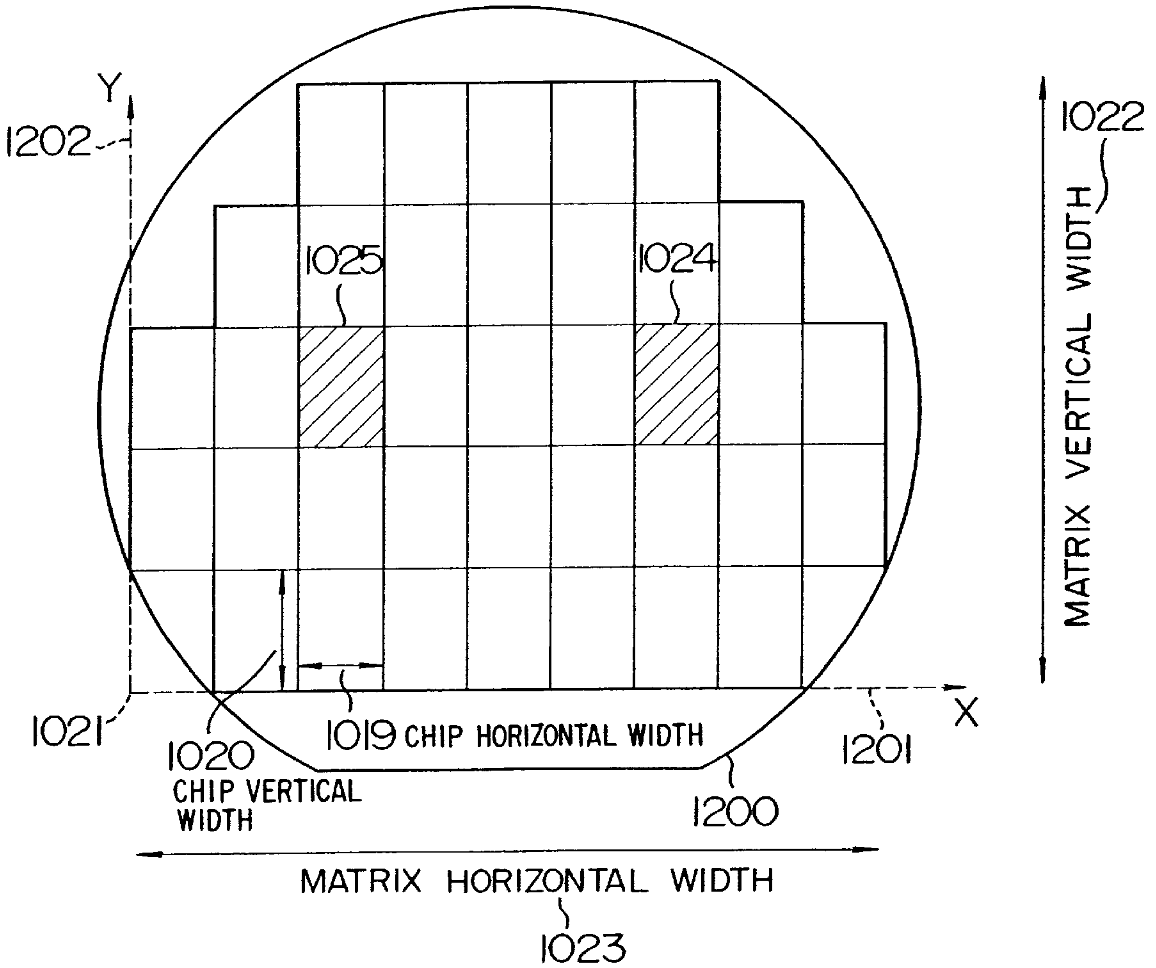
FIG. 6 is a view showing how to set a particle coordinate system.

When the wafer is inspected, the probing tester 7 receives probing management data input by the keyboard 1148 or the bar-code reader 1149. The probing management data contains a type of the inspected wafer, a lot number, a wafer number, an inspection date and time, and an operator name. The probing tester 7 serves to test an electric characteristic of a chip on the inspected wafer and save the probing test data consisting of the inspected result and the location of the chip together with the probing management data. The coordinate system shown in FIG. 6 is used for showing the location of the chip. When the probing tester 7 finishes the inspection of one slot, the probing test data analysis station 8 reads the probing management data and the probing test data of the inspected lot from the probing tester 7. Then, it serves to determine if the product is defective on the basis of the probing test data and register the result in the probing database 1154 as shown in FIG. 48. The probing database 1154 includes two data tables, that is, a probing test lot data table (see FIG. 48A) for the probing management data 1146 to 1150 except the wafer number and a probing test wafer data table (see FIG. 48B) for the lot number 1151, the wafer number 1150, and the probing test data 1153 to 1156.

The arrangement of the particle database 1010 is same as that described previously.

The particle data processing unit 1009 includes an analysis data auxiliary file shown in FIG. 49, a map information file described previously, and a product unit lot number management file. The analysis data auxiliary file contains the estimated product number 1158 per wafer registered in each product. The function of the product unit lot number management file is generally same as that described previously, except that when the product unit lot number becomes zero, the data about the product is deleted from the analysis auxiliary file.

The way to use the particle data analysis station 2 is generally the same as that previously described, except for additional analysis functions which are described hereinafter.

Figure 50:
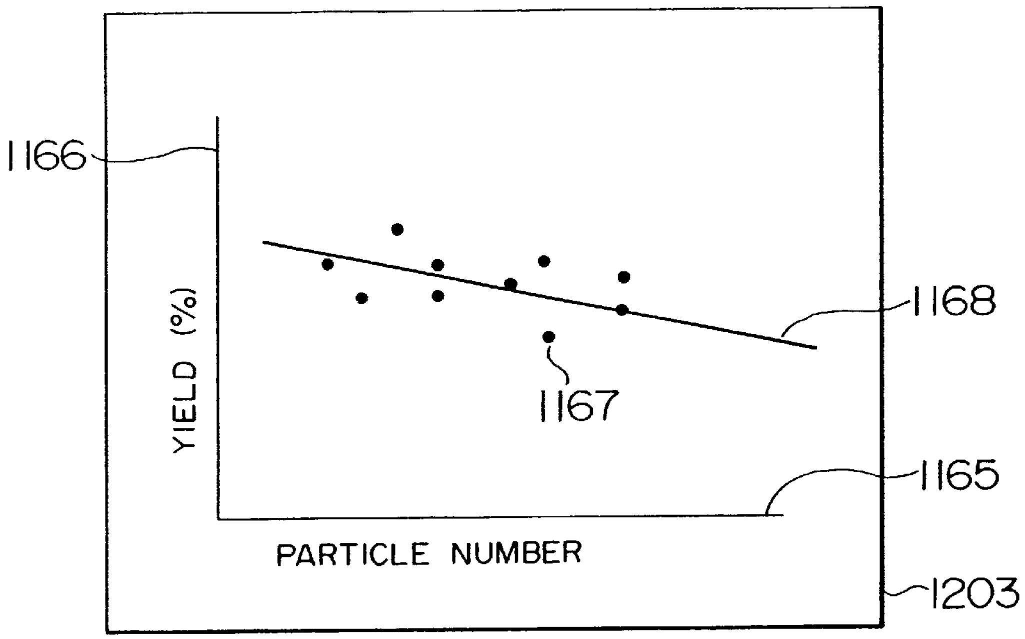
FIG. 50 is a chart showing correlation analysis between the amount of particles in number and the yield of chips, which is used for setting a reference value for management of the analysis process.

Next, the description will be directed to correlation analysis relating to a particle yield with reference to FIG. 50.

Figure 51:
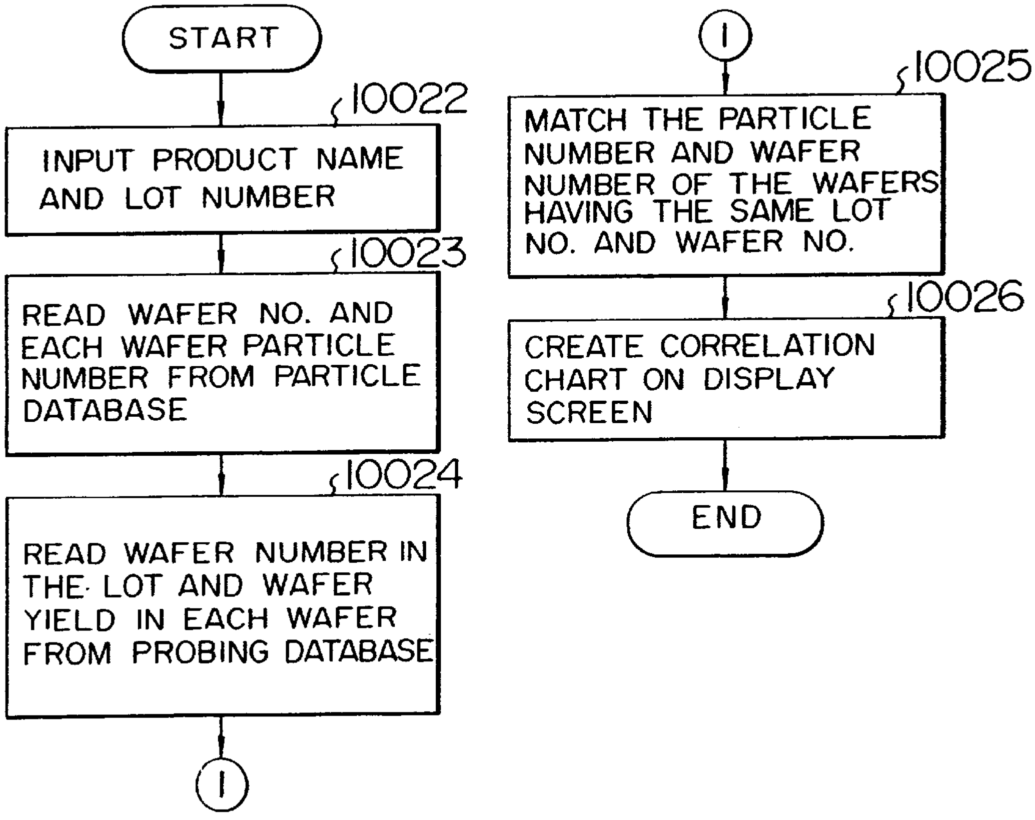
FIG. 51 is a flowchart for deriving correlation between the particle number and the yield.

The present operation serves to output as a correlation chart the relation between the particle number existing on a wafer being processed and a probing test yield given after the wafer processing process is over. The algorithm for the data analysis is illustrated in FIG. 51.

An analysis operator specifies a product name and a lot number (step 10022). By the specification, it is possible to save the wafer number of the specified lot and the particle number of each wafer in the internal memory 1118 from the particle database 1010 (step 10023) and yields of wafers in the specified lot in the memory 1118 from the probing data test station 8 (step 1024). The particle data processing unit 1009 serves to match the particle number to the wafer yield according to the wafer number (step 10025) and create the correlation chart (step 10026). As an output format, the abscissa 1165 denotes the particle number and the ordinate 1166 denotes the yield represented by a percent unit. Several dots 1167 are provided for calculating a primary regression line 1158 and depicting it on the chart.

Figure 52:
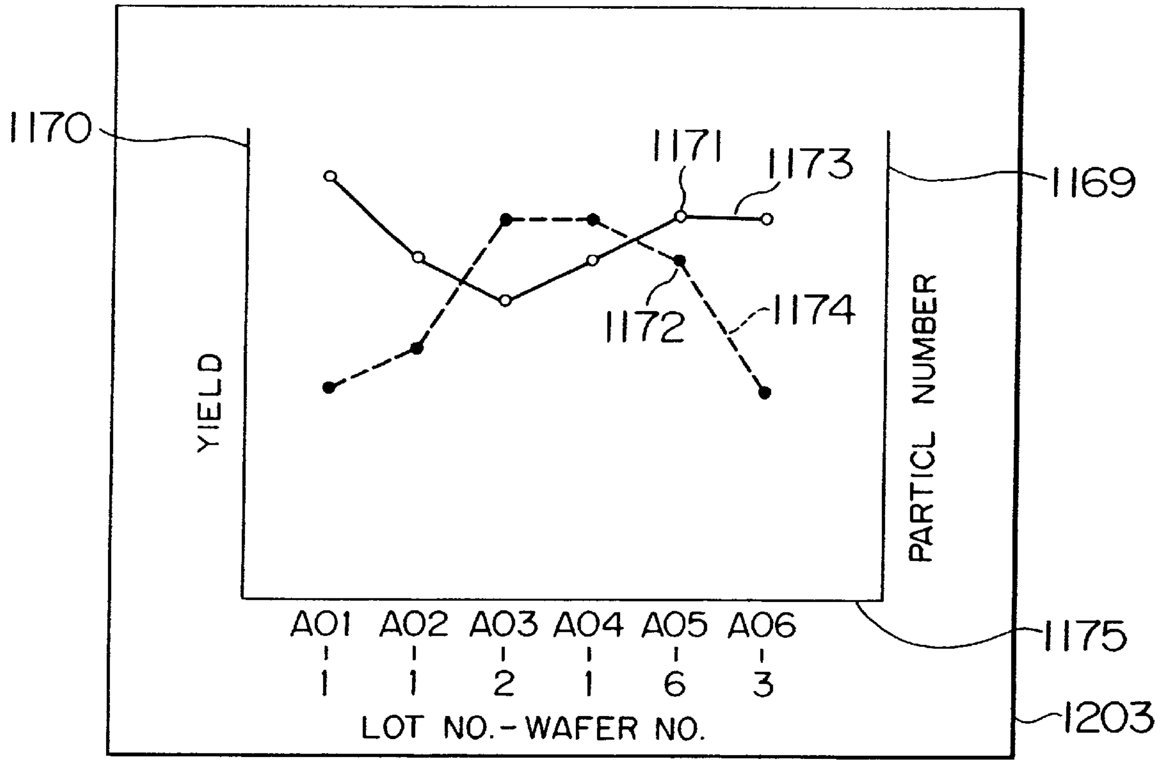
FIG. 52 is a chart showing an overlay trend between the particle number and the yield.

Next, the description will be directed to an analysis with reference to FIG. 52, which is referred to as particle yield overlay trend.

The present operation is designed to output as polygons a trend about the number of particle existing on a wafer being manufactured and a trend about a probing test yield of the manufactured wafer.

An analysis operator has to specify a product name and an inspection period and may specify a lot number if necessary. By the specification, it is possible to save an inspection date 5005, an inspection time 5006, a wafer number 5009, and a particle number 5010 of the lot matching to a retrieval condition shown in FIG. 5 in the internal memory 1118 from the particle database 1010 and the probing data of the wafer in the internal memory 1118 from the probing test data analysis station 8. The particle data processing unit 1009 serves to sort the wafers in earlier order on the basis of the inspection date and time. As an output format, the abscissa 1175 denotes the wafer numbers, which are ranged from the left. The righthand ordinate 1169 denotes a particle number and the left-hand ordinate 1170 denotes a wafer yield. The dots 1171 indicating the number of particles existing on the same wafer and the dots 1172 indicating yields are given on the same vertical axis so that both of those dots are connected for creating two polygons 1173, 1174. Two polygons have respective colors or kinds of polygons.

Figure 53:
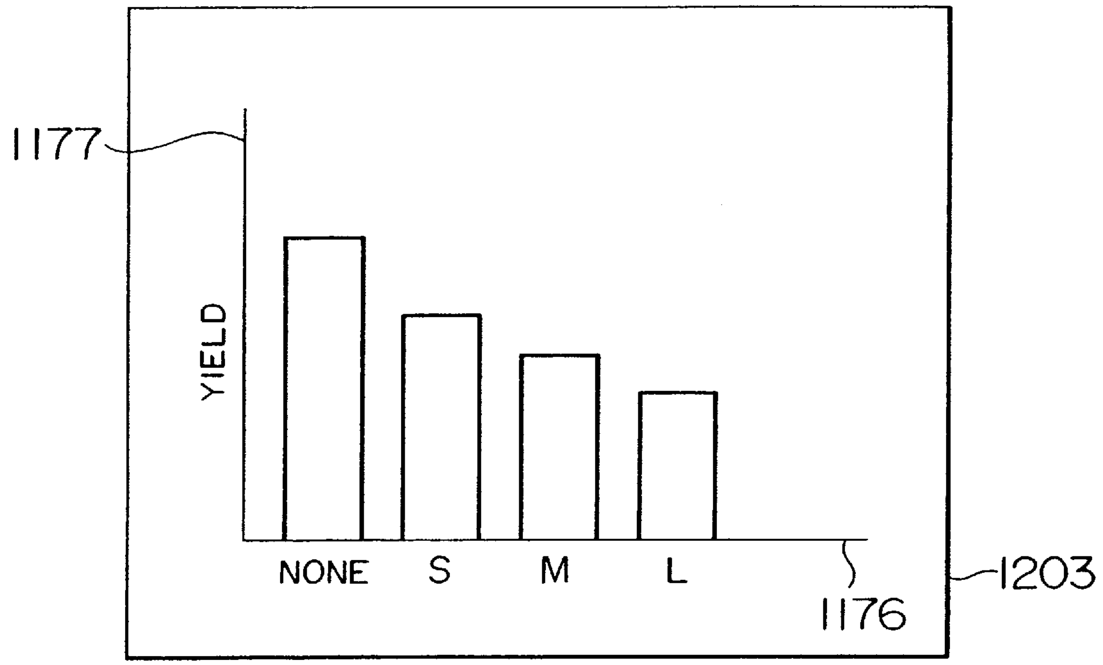
FIG. 53 is a chart showing a yield for each particle diameter size.

Next, the description will be directed to an analysis with reference to FIG. 53 which is referred to as a yield for each particle size.

The present operation is designed to output as a bar-chart the relation between a particle size on a wafer being manufactured and a probing test yield of the manufactured wafer.

An analysis operator has to specify a product name, a process name, and a lot number. By the specification, it is possible to save a wafer number in the specified lot, particle location coordinates 5014, 5015 on each wafer, and a particle size 5016 in the internal memory from the particle database 1010 and a wafer number in the specified lot and a determined result, good or defective, of each chip existing on the wafer from the probing test data station 8. The particle size is categorized into three classes of L, M, and S in order as described previously.

The particle data processing unit 1009 serves to determine the particle chips existing on each wafer and record their particle sizes on the basis of the chip arrangement information and the particle location coordinates. For doing so, the particle data processing unit 1009 employs the particle chip determining algorithm as described previously. For recording the particle size, if two or more particles exist on one chip, the largest particle size is representatively used. The chips are categorized into four classes of L-, M-, and S-sized particle chips and no particle chips. For each class, a yield is derived. In the present embodiment, the yield is defined for each particle size by the following equation:

yield for particle size=the number of goods in a particle chip for each particle size/the number of particle chips for each particle size×100

On the CRT 1013 as an output form, the abscissa 1176 denotes the particle sizes, which are ranged from no particles, S-sized particles, M-sized particles, and L-sized particles from the left. The ordinate 1177 denotes a yield for each particle size, which is displayed on each particle size denoted by the axis of abscissa of the bar chart.

Figure 54:
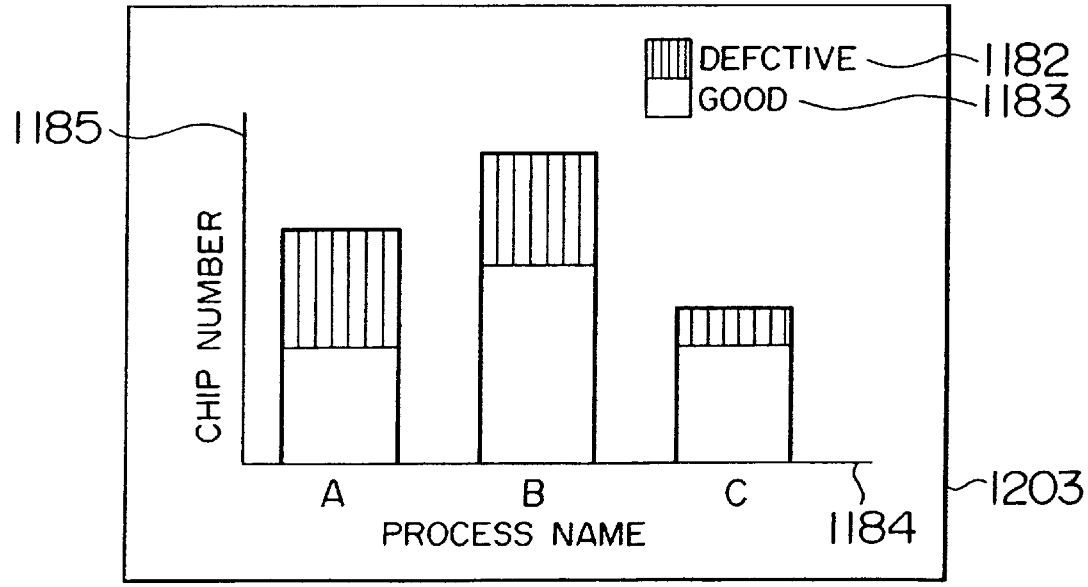
FIG. 54 is a chart showing a fraction defective in each sample processes.

Next, the description will be directed to an analysis with reference to FIG. 54 which is referred to as a fraction defective in each process in which particles are attached on a wafer (referred to as a particle process). The present operation is designed to output a probing test yield of the manufactured wafer in each particle process as a bar chart form.

An analysis operator has to specify a product name, two or more process names, and a lot number. By the specification, it is possible to save the inspection date 5005 and the inspection time 5006 as shown in FIG. 5, a wafer number 5013 of the lot, and particle location coordinates 5014, 5015 on each wafer in the internal memory from the particle database 1010 and the wafer number of the lot and the determined result, good or defective, of each chip in the wafer in the internal memory from the probing test data analysis station 8.

The particle data processing unit 1009 serves to create a particle extracting map for each process as described previously. For the particle extracting map for each process, the particle-attached chip determining algorithm is used for determining if the particles are attached on each chip. The unit 1009 serves to count the number of the particle-attached chips for each process and the number of good chips existing in the number of particle-attached chips. The output is displayed in the CRT 1013, in which the abscissa 1184 denotes the process names ranged in earlier order from the left and the ordinate 1185 denotes the chip number. For each process A, B, or C, the bar chart indicating the number of the particle-attached chips is created. The bar chart is categorized into two layers in which the lower layer denotes the number of good chips 1183 contained in the particle-attached chip and the upper layer denotes the number of defective chips 1182 contained therein. These layers have respective colors and meshes.

An embodiment which includes the visual inspection machine 4, the defect data analysis station 5, the probing tester 7, and the probing test data analysis station 8 in the inspection data analysis system is described with reference to FIG. 55. This embodiment substantially employs the arrangement of the system described in FIG. 44, except that the visual inspection machine 4 and the defect data analysis station 5 are employed in place of the particle inspection machine 1 and the particle data analysis station 2. The visual inspection machine 4 is quite identical to the visual inspection machine 4. The defect data analysis station 5 includes the arrangement of the defect data analysis station 5 described in FIG. 37 as well as an external communication unit 1189 for communicating with the probing data analysis station 8 (see FIG. 56).

The data to be inputted in or outputted from the probing tester 7 is identical to that described with reference to FIG. 44. The defect database 1111 has the same arrangement of that described in FIG. 38.

Figures 7, 8, 9:
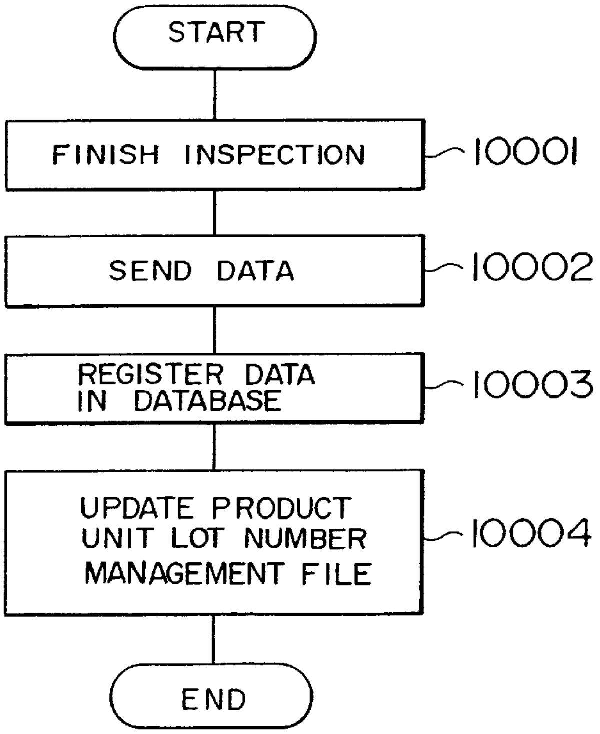
FIG. 7 is a chart showing arrangement of a map information file for each product.
FIG. 8 is a chart showing arrangement of a lot number managing file for each product.
FIG. 9 is a flowchart showing the procedure involved with registration of data.

The defect data processing unit 1110 includes the analysis data auxiliary file shown in FIG. 39, the map information file shown in FIG. 7, and the product unit wafer number management file, which is generally same as that shown in FIG. 8 except that if the product unit wafer number becomes zero, the data about the product kind is deleted from the analysis data auxiliary file.

As to how to use the defect data analysis station 5, it is the same as how to use the defect data analysis station 5 described previously, except that the content of the analysis function icon has an additional analysis function.

Next, the description will be directed to an analysis, which is referred to as a defect yield correlation analysis.

The present operation is generally the same as that designed to analyze the particles using the inspection data analysis system described previously, while the present embodiment is designed to analyze the defects using the inspection data analysis system.

Next, the description will be directed to analysis which is referred to as visual yield overlay trend.

This operation is generally the same as that designed to analyze the particles using the particle probing test system, while the present operation is designed to analyze the defects using the visual probing test system. In FIG. 52, the right-hand ordinate 1169 denotes a defect number, the left-hand ordinate 1170 denotes a yield, and the abscissa 1175 denotes a lot number and a wafer number.

Next, the description will be directed to an analysis, which is referred to as a yield for each kind of defect.

This operation is generally the same as that designed to analyze the particles using the particle probing test system, while the present operation is designed to analyze the defects using the visual probing test system. The present embodiment treats the category of defects in place of the category of a particle size. In the present embodiment, as shown in FIG. 53, the ordinate 1177 denotes a yield, and the abscissa 1176 denotes defect kinds, which are ranged in the order of pattern defects, particle defects, and the other defects.

Next, the description will be directed to an analysis, which is referred to as a yield for each defective process.

The present operation is generally the same as that designed to analyze the particles using the particle probing test system, while the present operation is designed to analyze the defects using the visual probing test system. In the present embodiment, as shown in FIG. 54, the ordinate 1185 denotes the chip number and the abscissa 1184 denotes the process name.

As to how to categorize the defects, the defects are categorized into a cause of defects, a defects-causing phenomenon, and a kind of defects. The cause of defects can be categorized into a resist residue, a fingerprint, a reticle, a pattern defect resulting from an reticle error, a pattern defect resulting from a resolution error, a discoloration defect resulting from over oxidation, and the other. The defects-causing phenomenon can be categorized into a pattern defect resulting from Al corrosion, a pattern defect resulting from a filled contact hole, a discoloration defect resulting from a pin hole, and the other. The kind of defects can be categorized into a pattern defect, a discoloration defect, a flaw, or other types of defects. The defects are categorized in accordance with the foregoing categories in order to perform the data analysis previously described.

The subject matter of FIG. 57 concerns a wafer manufacturing line on which the features previously described are used. This wafer manufacturing line is designed to set particle inspection processes immediately after the manufacturing process on which the particles are often caused, the process on which the manufacturing machine is adjusted, and the like. And, it sets a reference for a particle number per wafer to each particle inspection process. The particle data analysis station 2 serves to analyze the particle inspection result in the manner described previously, monitor the change of the particle number on time in each particle inspection process, and pick up the process having a higher particle number than the reference particle number. By the analysis described previously, the station 2 serves to pick up the process on which the sensed particle number is larger than that in any other process. After a m-th particle inspection process is picked up, the station 2 serves to select several manufacturing processes around the manufacturing process immediately before the m-th particle inspection process and set the m-th particle inspection process immediately after the manufacturing process (see FIG. 57). The defects data analysis station 5 serves to analyze the visual inspection result in the manner described previously.

Figure 58:
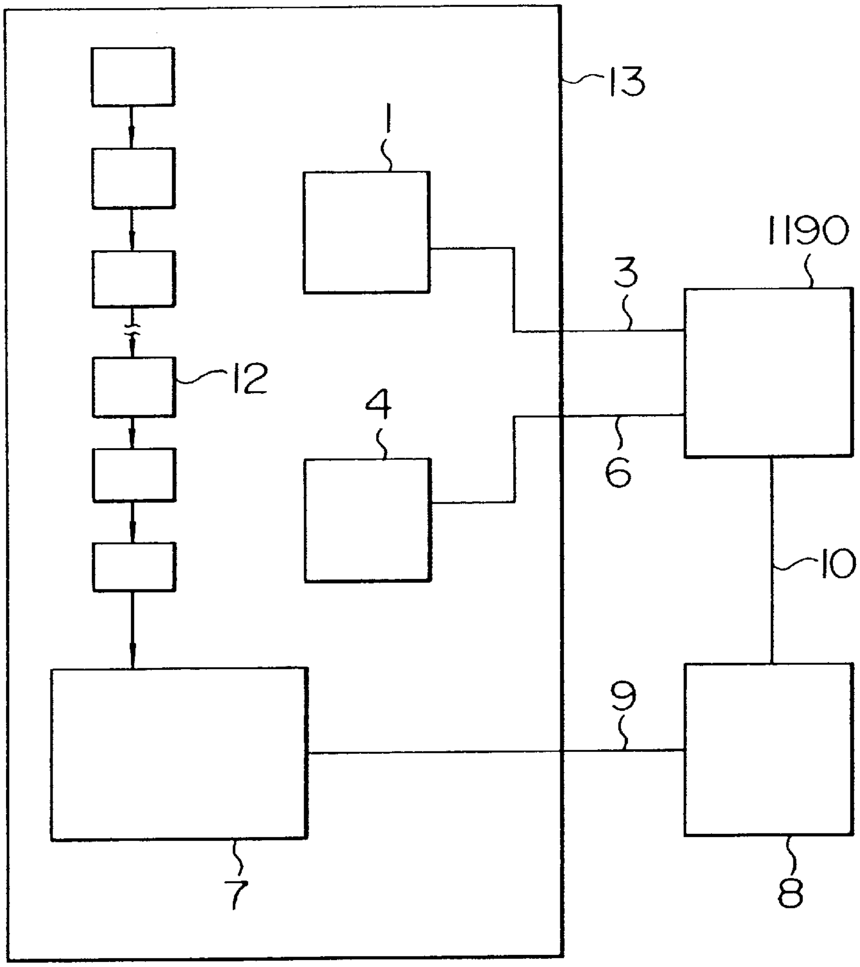
FIG. 58 is a diagram showing an overall system according to another embodiment of the present invention.
Figure 59:
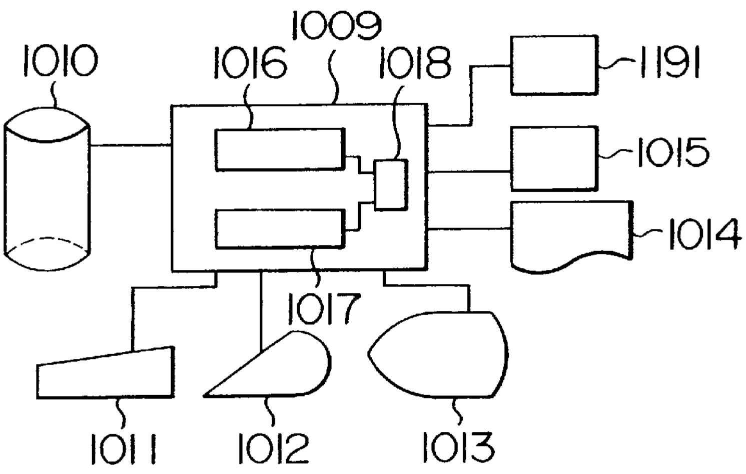
FIG. 59 is a diagram showing a data analysis station included in the system shown in FIG. 58.

The foregoing embodiment relating to FIG. 1 has been designed to individually provide the particle data analysis station 2 and the defects data analysis station 5, though, it is possible to integrate them into one workstation. The overall arrangement of FIG. 1 will be illustrated in FIG. 58.

Figure 47:
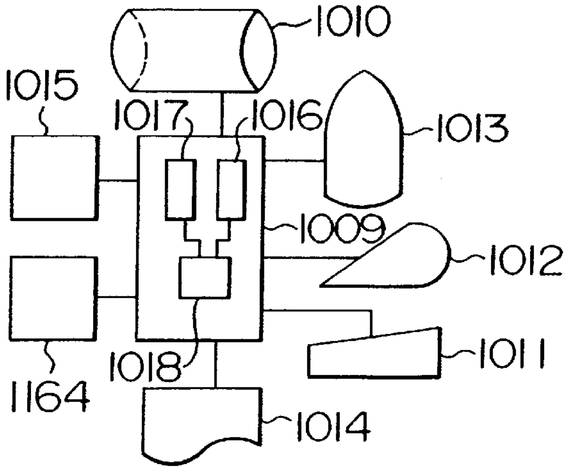
FIG. 47 is a diagram showing arrangement of the particle data analysis station.

The arrangement of the component unit is equal to those shown in FIGS. 3, 36, 45, and 46, except that the data analysis station 1190 includes an external communication unit 1191 for communicating with the visual inspection machine 4 and the particle data analysis station 2 shown in FIG. 47.

Figure 60:
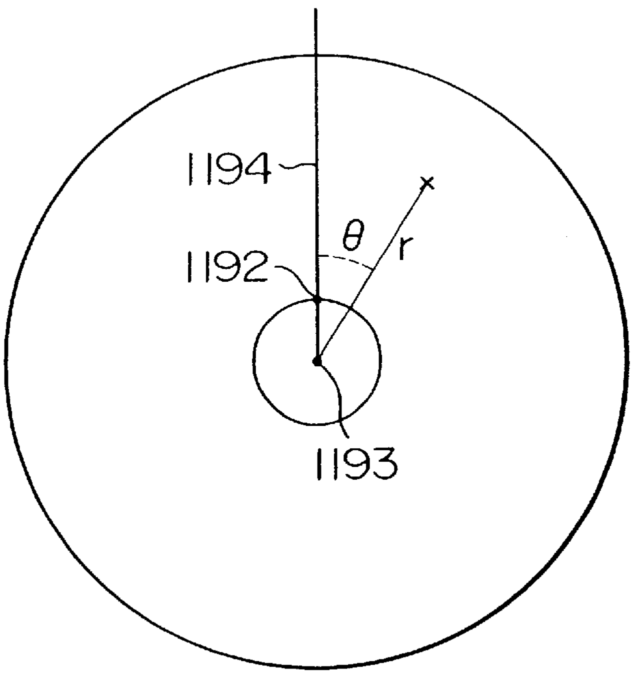
FIG. 60 is a view showing how to set a coordinate system when a magnetic disk is to be inspected.

The present invention may be applied to a magnetic disk production line. In the hardware arrangement shown in FIG. 1, the present invention employs a disk particle inspection machine in place of the particle inspection machine 1, a disk particle analysis station in place of the particle data analysis station 2, a disk visual inspection machine in place of the visual inspection machine 4, a disk defects analysis station in place of the defects data analysis station 5, a disk finished product inspection machine in place of the probing tester 7, and a disk product data analysis station in place of the probing data analysis station 8. The function of the inspection machine and the data analysis station is same as that described in the foregoing embodiments 2 to 37. Then, how to set location coordinates on a magnetic disk is described with reference to FIG. 60. On one part of the inner peripheral portion is attached a mark 1192 in the first magnetic disk manufacturing process. Assuming that the line connecting between a disk center 1193 and the mark is a reference line 1194, a two-dimensional polar coordinate system on a magnetic disk is set using the disk center and the reference line. Using the polar coordinate system, it is possible to carry out the functions such as the analysis, the operation, and the processing as described previously. As an output form, nothing corresponding to the border 1055 of the semiconductor chip is output.

Figure 61:
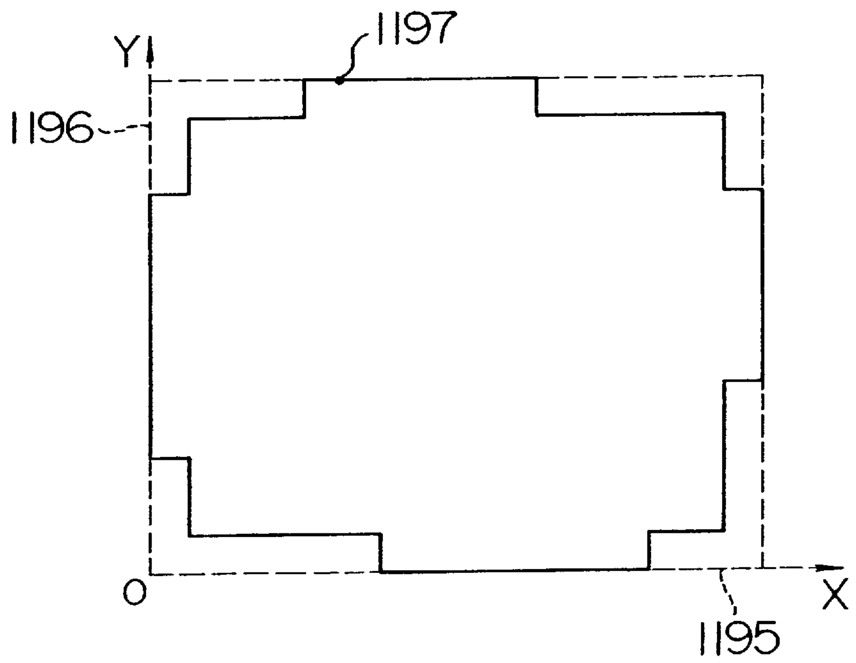
FIG. 61 is a view showing how to set a coordinate system when a circuit substrate is to be inspected.

The present invention is also applied to a substrate production line. In the hardware arrangement shown in FIG. 1, the present embodiment employs a substrate particle inspection machine in place of the particle inspection machine 1, a substrate particle analysis station in place of the particle data analysis station 2, a substrate visual inspection machine in place of the visual inspection machine 4, a substrate defects analysis station in place of the defects data analysis station 5, a substrate final inspection machine in place of the probing tester 7, and a substrate data analysis station in place of the probing data analysis station 8. The functions of the inspection machine and the data analysis station are basically same as those described previously. The present embodiment employs the steps of setting a minimum square enclosing a work as shown in FIG. 61, a mark 1197 on the work as a reference point, and an X-axis 1195 and a Y-axis 1196. Using this coordinate system, this embodiment serves to perform the analysis described previously.

According to the present invention, it has been described that the relation between the defects and the product character is conventionally derived by taking the correlation between the defect density and the yield on a wafer basis. Since, however, the data can be analyzed on a chip basis, the present invention is capable of grasping the relation between the defects causing condition of each chip and the product character of the chip, resulting in enabling new analysis of the data and elucidating the causal relation between the defects (cause) and the product character (result). This function contributes to providing effective decision materials for properly improving yields. Further, by individually using the particle inspection machine and the visual inspection machine, the inspection speeds of which are different, this invention has a new function of determining a process to be visually inspected in the mass production line from the particle inspection result. In addition, it has an advantage that it is unnecessary to match the particle inspection data to the defects inspection data in the overall process and machines.

The present invention is designed to formalize the operating method and the data retrieval routine in the analysis station and generalize the data analysis method. Hence, it is capable of easily knowing an abnormality-caused process and the content of the abnormality, so that a person in charge of the manufacturing machine can take rapid measures for the abnormality.

The present invention establishes a novel method for analyzing defects resulting from the product defect. This invention can be applied to the manufacturing line of a product (for example, a magnetic disk or a substrate) requiring visual inspection and final product inspection of the work.

We claim:

1. An electronic device inspection system comprising:

a first inspection machine for inspecting defects on a workpiece comprised of an electronic device; and a first analysis unit comprising receiving means for receiving first defect information determined by the inspection performed by the first inspection machine, memory means for memorizing the first defect information received by the receiving means, analysis means for analyzing the first defect information memorized by the memory means, and output means for outputting a result based on the analysis performed by the analysis means, wherein the first analysis unit includes means for communicating with a second separate analysis unit which separately stores second defect information pertaining to electrical characteristics of at least a chip of the workpiece.

2. An electron device inspection system according to claim 1, wherein said electrical characteristics are determined by an electrical characteristic tester coupled to said second separate analysis unit.

3. An electron device inspection system according to claim 2 wherein the electrical characteristic tester is arranged to test a wafer in final product form.

4. An electron device inspection system according to claim 2, wherein the electrical characteristic tester is a probe tester.

5. An electronic device inspection system comprising:

a visual inspection machine to inspect defects on a workpiece comprised of an electronic device and to provide first defect information regarding the defects as an output;

a particle inspection machine to inspect defects on the workpiece and to provide second defect information regarding the defects as an output; and a first processor coupled to receive the first defect information from the visual inspection machine and the second defect information from the particle inspection machine, wherein a first analysis on the basis of at least one of the first defect information and the second defect information is processed in said first processor and wherein the first processor includes means for communicating with a second separate processor which separately stores information pertaining to electrical characteristics of at least a chip of the workpiece.

6. An electron device according to claim 5, wherein said electrical characteristics are determined by an electrical characteristic tester coupled to said second separate processor.

7. An electron device according to claim 6, wherein the electrical characteristics tester is arranged to test a wafer in final product form.

8. An electron device according to claim 6, wherein the electrical characteristic tester is a probe tester.

9. An electronic device inspection system for memorizing and analyzing defect inspection information of a workpiece separate from electrical characteristic test information comprising:

a first inspection machine for inspecting defects on a workpiece comprised of an electronic device; and a first analysis unit comprising receiving means for receiving first defect information determined by the inspection performed by the first inspection machine, memory means for memorizing the first defect information received by the receiving means, analysis means for analyzing the first defect information memorized by the memory means, and output means for outputting a result based on the analysis performed by the analysis means, wherein said memorizing and analyzing of said first defect information is carried out in said first analysis unit separate from analysis of electrical characteristics performed in an external analysis unit.

10. An electron device according to claim 9, wherein said electrical characteristics are determined by an electrical characteristic tester coupled to said external analysis unit.

11. An electron device according to claim 10, wherein the electrical characteristics tester is arranged to test a wafer in final product form.

12. An electron device according to claim 10, wherein the electrical characteristic tester is a probe tester.

13. An electronic device inspection system for memorizing and analyzing defect inspection information of a workpiece separate from electrical characteristic test information comprising:

a visual inspection machine to inspect defects on a workpiece comprised of an electronic device and to provide first defect information regarding the defects as an output;

a particle inspection machine to inspect defects on the workpiece and to provide second defect information regarding the defects as an output; and a first processor coupled to receive the first defect information from the visual inspection machine and the second defect information from the particle inspection machine;

wherein a first analysis on the basis of at least one of the first defect information and the second defect information stored in the first processor is processed by said first processor carried out separate from analysis of electrical characteristics stored in an external processor.

14. An electron device according to claim 3, wherein said electrical characteristics are determined by an electrical characteristic tester coupled to said external processor.

15. An electron device according to claim 14, wherein the electrical characteristics tester is arranged to test a wafer in final product form.

16. An electron device according to claim 14, wherein the electrical characteristic tester is a probe tester.

17. An electronic device inspection system comprising:

a first inspection machine for inspecting defects on a workpiece comprised of an electronic device; and a first analysis unit comprising receiving means for receiving first defect information determined by the inspection performed by the first inspection machine, memory means for memorizing the first defect information received by the receiving means, analysis means for analyzing the first defect information memorized by the memory means, and output means for outputting a result based on the analysis performed by the analysis means, wherein the first analysis unit includes means for receiving an output of a second separate analysis unit which separately receives, memorizes and analyzes second defect information obtained by an electrical characteristic tester pertaining to electrical characteristics of at least a chip of the workpiece.

18. An electronic device inspection system comprising:

a visual inspection machine to inspect defects on a workpiece comprised of an electronic device and to provide first defect information regarding the defects as an output;

a particle inspection machine to inspect defects on the workpiece and to provide second defect information regarding the defects as an output; and a first processor coupled to receive the first defect information from the visual inspection machine and the second defect information from the particle inspection machine, wherein a first analysis on the basis of at least one of the first defect information and the second defect information is processed in said first processor and wherein the first processor includes means for receiving an output of a separate processor which separately receives, memorizes and analyzes information obtained by an electrical characteristic tester pertaining to electrical characteristics of at least a chip of the workpiece.

19. An electron device according to claim 18, wherein the electrical characteristic tester is a probe tester.

20. An electronic device inspection and defect analysis system comprising:

a first inspection machine for inspecting defects on a workpiece comprised of an electronic device; and a defect analysis unit for analyzing defects separately from any analysis carried out by any external analysis unit of electrical characteristics of at least a chip of the "work-piece" determined by a tester from the workpiece, said defect analysis unit comprising receiving means for receiving first defect information determined by the inspection performed by the first inspection machine, memory means for memorizing the first defect information received by the receiving means, analysis means for analyzing the first defect information memorized by the memory means, and output means for outputting a result based on the analysis performed by analysis means.

21. An electronic device inspection and defect analysis system according to claim 20, wherein the defect analysis unit includes means for communicating with a separate electrical characteristic analysis unit which separately analyzes electrical characteristics determined from the workpiece by an electrical characteristic tester.

22. An electronic device inspection and defect analysis system according to claim 21, wherein the electrical characteristic tester is a probe tester.

23. An electronic device inspection and defect analysis system comprising:

a visual inspection machine to inspect defects on a workpiece comprised of an electronic device and to provide first defect information regarding the defects as an output;

a particle inspection machine to inspect defects on the workpiece and to provide second defect information regarding the defects as an output; and a defect processor for analyzing defects separately from any analysis carried out by any external analysis unit of electrical characteristics of at least a chip of the "work-piece" determined by a tester from the workpiece, said defect processor being coupled to the visual inspection machine and the particle inspection machine.

24. An electronic device inspection and defect analysis system according to claim 23, wherein said defect processor includes means for communicating with a separate electrical characteristic processor which analyzes electrical characteristics determined from the workpiece by an electrical characteristic tester.

25. An electronic device inspection and defect analysis system according to claim 24, wherein the electrical characteristic tester is a probe tester.

* * * * *